United States Patent [19]
Jankowiak et al.

[11] Patent Number: 5,898,493
[45] Date of Patent: Apr. 27, 1999

[54] CAPILLARY ELECTROPHORESIS-FLUORESCENCE LINE NARROWING SYSTEM (CE-FLNS) FOR ON-LINE STRUCTURAL CHARACTERIZATION

[75] Inventors: Ryszard J. Jankowiak; Gerald J. Small, both of Ames, Iowa; Peter A. Shields, Reading, Mass.

[73] Assignee: Iowa State University Research Foundation, Inc., Ames, Iowa

[21] Appl. No.: 08/870,952

[22] Filed: Jun. 6, 1997

Related U.S. Application Data

[60] Provisional application No. 60/019,276, Jun. 7, 1996.

[51] Int. Cl.$^6$ .................................................. G01N 21/03
[52] U.S. Cl. ......................... 356/318; 356/246; 356/344
[58] Field of Search .................................. 356/317, 318, 356/417, 344, 246; 204/601, 603

[56] References Cited

PUBLICATIONS

X.C. Huang et al., "Capillary Array Electrophoresis Using Laser–Excited Confocal Fluorescence Detection", *Anal. Chem.*, 64, pp. 967–972 (1992).

R. Jankowiak et al., "Capillary Electrohphoresis—Fluorescence Line–Narrowing System for On–Line Structural Characterization of Molecular Analytes", *Anal. Chem.*, 68, pp. 2549–2553 (1996).

R. Jankowiak et al., "Capillary Electrophoresis—Fluorescence Line–Narrowing System for On–Line Structural Characterization of Molecular Analytes", *Chemical Abstracts.*, 125, p. 1304, Ref.No. 125:131244e (1996).

R. Jankowiak et al., "Fluorescence Line Narrowing: A High–Resolution Window on DNA and Protein Damage from Chemical Carcinogens", *Chem. Res. Toxicol.*, 4, pp. 256–269 (1991).

R. Jankowiak et al., "Fluorescence Line Narrowing—Nonphotochemical Hole Burning Spectrometry: Femtomole Detection and High Selectivity for Intact DNA—PAH Adducts", *Chem. Res. Toxicol*, 1, pp. 60–68 (1988).

R. Jankowiak et al., "Laser Spectroscopic Studies of DNA Adduct Structure Types from Enantiomeric Diol Epoxides of Benzo[a]pyrene", *Chem. Res. Toxicol*, 3, pp. 39–46 (1990).

R. Jankowiak et al., "Spectral Hole–Burning Spectroscopy in Amorphous Molecular Solids and Proteins", *Chem Rev.*, 93, pp. 1471–1502 (1993).

C.E. Kientz et al., "Eluent Jet Interface for Combining Capillary Liquid Flows with Electron Impact Mass Spectrometry", *Anal. Chem.*, 68, pp. 675–681 (1996).

W.–H. Kim et al., "Hyperquenched Glassy Films of Water: A Study by Hole Burning", *J. Phys. Chem.*, 99, pp. 7300–7310 (1995).

W.G. Kuhr, "Capillary Electrophoresis", *Anal. Chem.*, 62, pp. 403 R–414 R (1990).

T.T. Lee et al., "High–Sensitivity Laser–Induced Fluorescence Detection of Native Proteins in Capillary Electrophoresis", *Journal of Chromatography*, 595, pp. 319–325 (1992).

T.T. Lee et al., "Quantitative Determination of Native Proteins in Individual Human Erythrocytes by Capillary Zone Electrophoresis with Laser–Induced Fluorescence Detection", *Anal. Chem.*, 64, pp. 3045–3051 (1992).

(List continued on next page.)

*Primary Examiner*—Richard A. Rosenberger
*Attorney, Agent, or Firm*—Meuting, Raasch & Gebhardt, P.A.

[57] ABSTRACT

Capillary electrophoresis (CE) is interfaced with low temperature fluorescence line-narrowing (FLN) spectroscopy for on-line structural characterization of separated molecular analytes.

29 Claims, 12 Drawing Sheets

PUBLICATIONS

K.-M. Li et al., "Identification and Quantitation of Dibenzo[a,l]pyrene–DNA Adducts Formed by Rat Liver Microsomes in Vitro: Preponderance of Depurinating Adducts", *Biochemistry*, 34, pp. 8043–8049 (1995).

L. Licklider et al., "On–Line Microreactors/Capillary Electrophoresis/Mass Spectrometry for the Analysis of Proteins and Peptides", *Anal. Chem.*, 67, pp. 4170–4177 (1995).

I.S. Lurie, "Analysis of Seized Drugs by Capillary Electrophoresis", *Analysis of Addictive and Misused Drugs*, edited by John A. Adamovics; Pub. by Marcel Dekker, Inc., New York, NY (1995), pp. 151–219.

R.E. Milofsky et al., "Native Fluorescence Detection of Nucleic Acids and DNA Restriction Fragments in Capillary Electrophoresis", *Anal. Chem.*, 65, pp. 153–157 (1993).

L. Nakhimovsky et al., "Handbook of Low Temperature Electronic Spectra of Polycyclic Aromatic Hydrocarbons", *Physical Science Data 40*, Table of Contents, pp. xi–xiii.

S. Nie et al., "Ultrasensitive Fluorescence Detection of Polycyclic Aromatic Hydrocarbons in Capillary Electrphoresis", *Anal. Chem.*, 65, pp. 3571–3575 (1993).

R.I. Personov, "Site Selection Spectroscopy of Complex Molecules in Solutions and Its Applications", *Spectroscopy and Excitation Dynamics of Condensed Molecular Systems*, North–Holland Publishing Company, Chapter 10, pp. 555–619 (1983).

E.G. Rogan et al., "Identification and Quantitation of Benzo[a]pyrene–DNA Adducts Formed in Mouse Skin", *Chem. Res. Toxicol.*, 6, pp. 356–363 (1993).

M.J. Sanders et al., "Identification of Polycyclic Aromatic Hydrocarbon Metabolites in Mixtures Using Fluorescence Line Narrowing Spectrometry", *Anal. Chem.*, 57, pp. 1148–1152 (1985).

J.B. Shear et al., "Automated Velocity Programming for Increased Detection Zone Residence Times in Capillary Electrophoresis", *Anal. Chem.*, 65, pp. 3708–3712 (1993).

J.B. Shear et al., "Optimizing Fluorescence Detection in Chemical Separations for Analyte Bands Traveling at Different Velocities", *Anal. Chem.*, 65, pp. 2977–2982 (1993).

Y. Shi et al., "Capillary Zone Electrophoresis of Neutral Organic Molecules in Organic—Aqueous Solution", *Journal of High Resolution Chromatography*, 17, pp. 713–718 (1994).

Y. Shi et al., "HPCZE of Nonionic Compounds Using a Novel Anionic Surfactant Additive", *Anal. Chem.*, 67, pp. 3023–3027 (1995).

M. Suh, "Conformational studies of the (+)–trans, (–)–trans, (+)–cis, and (–)–cis adducts of anti–benzo[a]pyrene diolepoxide to $N^2$–dG in duplex oligonucleotides using polyacrylamide gel electrophoresis and low–temperature fluorescence spectroscopy", *Biophysical Chemistry*, 56, pp. 281–296 (1995).

M. Suh et al., "Flanking Base Effects on the Structural Conformation of the (+)–trans–anti–benzol[a]pyrene diolepoxide adduct to $N^2$–dG in Sequence–Defined Oligonucleotides", *Carcinogenesis*, 15, pp. 2891–2898 (1994).

M. Suh et al., "Formation and Persistence of Benzo[a]pyrene–DNA Adducts in Mouse Epidermis in vivo: Importance of Adduct Conformation", *Carcinogenesis*, 16, pp. 2561–2569 (1995).

H.Swerdlow et al., "Three DNA Sequencing Methods Using Capillary Gel Electrophoresis and Laser–Induced Fluorescence", *Anal. Chem.*, pp. 2835–2841 (1991).

J. Tehrani et al., "Capillary Electrophoresis: An Integrated System with a Unique Split–Flow Sample Introduction Mechanism", *Journal of High Resolution Chromatography*, 14, pp. 10–14 (1991).

S. Terabe et al., "Electrokinetic Chromatography with Micellar Solution and Open–Tubular Capillary", *Anal. Chem.*, 57, pp. 834–841 (1985).

S. Terabe et al., "Electrokinetic Separations with Micellar Solutions and Open–Tubular Capillaries", *Anal. Chem.*, 56, pp. 111–113 (1984).

S. Terabe et al., "Separation of highly hydrophobic compounds by cyclodextrin–modified miceller eletrokinetic chromatography", *Journal of Chromatography*, 516, pp. 23–30 (1990).

I.B. Weinstein et al, "Benzo[a]pyrene Diol Epoxides as Intermediates in Nucleic Acid Binding in vitro and in vivo", *Science*, 193, pp. 592–594 (1976).

J.D. Winefordner et al., "Solvents for Phosphorimetry", *Analytical Chemistry*, 35, pp. 2211–2222, 2212 (1963).

D. Zamzow et al., "Capillary electrophoresis—fluorescence line narrowing (CE–FLN) system for DNA adduct characterization", from the book distributed at the Jun. 9–13 meeting of *DNA Adducts and Mutations in Human Biomonitoring*, Karolinska Institutet, Stockholm, Sweden (1996).

R. Jankowiak et al., "Conformational Studies of Stereoisomeric Tetrols Derived from syn– and anti–Dibenzo[a,l]pyrene Diol Epoxides", *Chemical Research in Toxicology*, 10, pp. 677–686 (1997).

D. Zamzow et al., "Capillary Electrophoresis—Fluorescence Line–Narrowing (CE–FLN) System for DNA Adduct Characterization", *Mol. Cryst. Liq. Cryst.*, 291, pp. 155–162 (1996).

C.A. Angell et al., "Glass–Forming Composition Regions and Glass Transition Temperatures for Aqueous Electrolyte Solutions", *The Journal of Chemical Physics*, 52, pp. 1058–1068 (1970).

F. Ariese et al., "Conformational Studies of Depurinating DNA Adducts from syn–Dibenzo[a,l]pyrene Diolepoxide", *Carcinogenesis*, 17, pp. 829–837 (1996).

R.S. Brown et al., "Cyclodextrin–Modified Capillary Electrophoresis: Determination of Polycyclic Aromatic Hydrocarbons in Contaminated Soils", *Anal. Chem.*, 68, pp. 287–292 (1996).

D. Chen et al., "Single–Molecule Detection in Capillary Electrophoresis: Molecular Shot Noise as a Fundamental Limit to Chemical Analysis", *Anal. Chem.*, 68, pp. 690–696 (1996).

D.B. Craig, "Detection of Attomolar Concentrations of Alkaline Phosphatase by Capillary Electrophoresis Using Laser–Induced Fluorescence Detection", *Anal. Chem.*, 68, pp. 697–700 (1996).

P.D. Devanesan et al., "Identification and Quantitation of 7,12–Dimethylbenz[a]anthracene—DNA Adducts Formed in Mouse Skin", *Chem. Res. Toxicol.*, 6, pp. 364–371 (1993).

B. Hogan et al., "Determination of Intracellular Species at the Level of a Single Erythrocyte via Capillary Electrophoresis with Direct and Indirect Fluorescence Detection", *Anal. Chem.*, 64, pp. 2841–2845 (1992).

B. Hogan et al., "Single–cell Analysis at the Level of a Single Human Erythrocyte", *Trends in Analytical Chemistry*, 12, pp. 4–9 (1993).

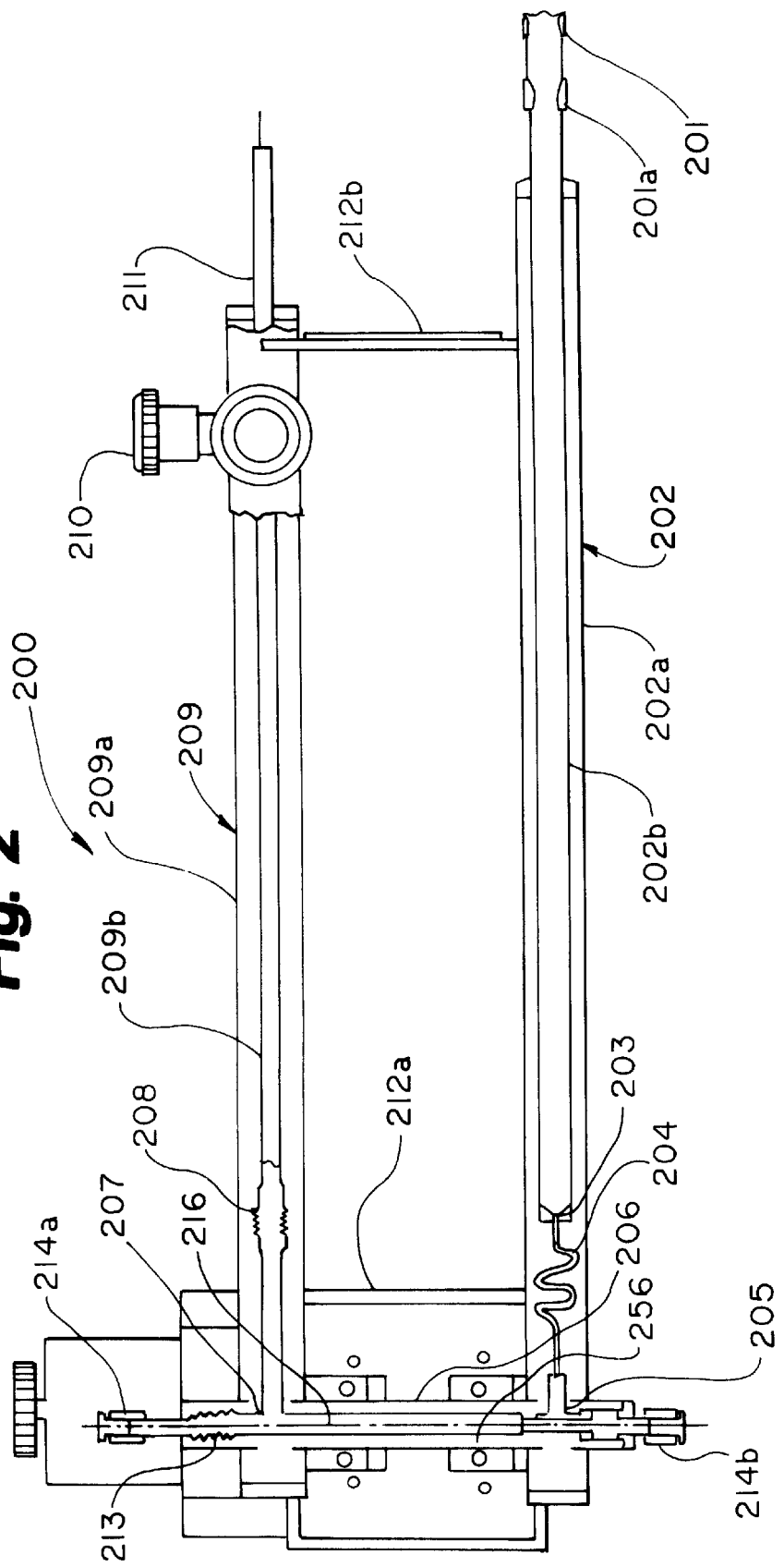

CAPILLARY ELECTROPHORESIS-FLUORESCENCE LINE NARROWING SYSTEM (CE-FLNS) FOR ON-LINE STRUCTURAL CHARACTERIZATION

This application claims the benefit of U.S. Provisional Application No. 60/019276, filed Jun. 7, 1996.

STATEMENT OF GOVERNMENT RIGHTS

This invention was made with government support under grants from the United States Department of Energy (Contract No. W-7405-Eng-82). The U.S. government has certain rights in this invention.

BACKGROUND OF THE INVENTION

Capillary electrophoresis (CE) is a widely used analytical and bioanalytical separation technique. It is also finding considerable use in biomedical research with new applications continually emerging. Capillary electrophoresis has been used for analysis of amino acids, peptides, proteins, nucleic acid bases, DNA oligonucleotides and numerous organic molecules. Both small ions and large biomolecules can be separated (J. Tehrani et al., High Res. Chrom., 14, 10–14 (1991)). Electrophoresis is a powerful approach for gene mapping (R. Milofsky et al., Anal. Chem., 65, 153–157 (1993)); X. Huang et al., Anal. Chem., 64, 967–972 (1992)) and DNA sequencing (H. Swerdlow et al., Anal. Chem., 63, 2835–2841 (1991)). Recently, the chemical analysis of individual cells by CE has attracted much attention (B. Hogan et al., Anal. Chem., 64, (1992); B. Hogan et al., Trends Anal. Chem., 12, 4–9 (1993)).

Polycyclic aromatic hydrocarbons (PAH) constitute a potent class of chemical carcinogens. The ability to analyze PAH in small volumes at attomole levels opens many opportunities for studying intracellular uptake, metabolism, and carcinogen-DNA adduct formation, all of which are important factors in mutagenesis and tumorigenesis. Various protocols for separation of PAH by CE have already been established. In micellar electrokinetic capillary chromatography, introduced by Terabe et al. (S. Terabe et al., Anal. Chem., 56, 111–116 (1984); S. Terabe et al., Anal. Chem., 57, 834–839 (1985); S. Terabe et al, J. Chrom., 516, 23–31 (1990)), micelles were used as a pseudophase. Nie et al. (S. Nie et al., Anal. Chem., 65, 3571–3575 (1993)) developed an approach based on solvophobic association of PAH analytes with tetraalkylammonium ions in a mixed acetonitrile-water solvent. Yan and coworkers (T. Lee, Anal. Chem., 64, 3045–3051 (1992)) demonstrated that capillary electrochromatography can be used for separation of priority PAH. Shi and Fritz (Y. Shi et al., Anal. Chem., 67, 3023–3027 (1995); Y. Shi et al, J High Res. Chrom, 117, 713 (1994)) established that excellent separation of PAH by CE can be achieved by the addition of sodium dioctyl sulfosuccinate (DOSS) to an acetonitrile-water electrolyte. Very recently, Brown et al. (R. S. Brown et al., Anal. Chem., 68, 287–292 (1996)) described a separation method for PAH using cyclodextrin-modified CE. All these approaches are able to detect PAH at sub-femtomole levels, a detectability required, for example, in the study of PAH-induced carcinogenesis.

In CE, analyte molecules are typically probed, i.e., detected, only briefly as they traverse detection zones located either on-line or in a post-column flow cell. The narrowness of this temporal detection window effectively limits the signal to noise ratio (J. Shear et al., Anal. Chem., 65, 3708–3712 (1993)). The most widely used detection method with CE is absorbance, which is usually shot-noise limited. Fluorescence, particularly laser-induced fluorescence (LIF), has also been used for detection, outperforming absorbance in sensitivity of detection by several orders of magnitude. However, the brief time available for determination of an analyte also poses a problem for LIF detection, especially when low intensity continuous wave (CW) lasers incapable of providing high induced absorption rates are used (J. Shear et al., Anal. Chem., 65, 2977–2982 (1993)). Zare and coworkers (J. Shear et al, Anal. Chem., 65, 3708–3712 (1993)) showed that velocity programming for increased detection zone residence times in CE is necessary to improve both the accuracy of quantitation and detection limits. The use of intense pulsed lasers in CE-LIF for the analysis of molecular analytes at ambient temperature produces a stronger detectable signal, but is accompanied by problem of analyte photodegradation.

Efforts to improve analyte resolution in CE are also important, particularly as detection sensitivity increases. In the case of CE-LIF, however, the emphasis has been on laser-induced fluorescence providing superior detection limits, i.e., analyte resolution is still provided by CE. At best, LIF with detection at ambient temperature can provide only very limited spectral resolution due to large vibronic fluorescence bandwidths (about 500 $cm^{-1}$). Resolution between monomethylated isomers of a PAH would, for example, have to be provided by the physical separation process of CE.

It is well-recognized that analysis of chemically complex samples often requires a two-step analytical approach (separation followed by analyte characterization). Research involving analytical separation methods such as high performance liquid chromatography (HPLC) and CE has been greatly advanced by recent efforts to couple these separation techniques with sensitive spectroscopic methods that go beyond simple detection of molecular analytes by producing structural information about the separated analytes. For example, HPLC has been coupled with NMR spectroscopy for direct analysis of complex mixtures from both synthetic and biological origins. Interfacing CE with mass spectroscopy (MS) has been demonstrated; and capillary zone electrophoresis coupled with electrospray MS has been used for separation and subsequent detection of DNA adducts. Capillary electrochromatography has been coupled to MS for analysis of pharmaceutical drugs.

The utility of laser-induced fluorescence detection of molecular analytes is well-established. However, its use as a detection method in CE has been limited by the brief time available for interrogation of an analyte, and, when pulsed lasers are used at ambient temperature, photodegradation of the separated analytes. Further, laser-induced fluorescence at ambient temperature does not provide structural information about the analytes of interest. There is, therefore, a need in the art for a system that successfully interfaces fluorescence spectroscopy with a capillary electrophoresis apparatus in a manner and under conditions that allow structural characterization of closely related analytes.

SUMMARY OF THE INVENTION

The present invention provides a system for use in capillary electrophoresis that utilizes a specially designed capillary cryostat containing an optically accessible sample chamber to facilitate low-temperature laser-induced fluorescence spectroscopic analysis of separated analytes. In addition to the capillary cryostat, the system includes a spectrally narrow excitation source, such as a laser, positioned to direct a beam of light into the interior of the capillary to induce fluorescence emission from the target species, and a wavelength-dispersive detection system positioned to detect fluorescence emission from the target species.

The capillary cryostat of the invention includes a capillary having a transparent annular wall forming the interior portion for placement of the target species, and a capillary encasement having a transparent portion that surrounds at least a portion of the transparent annular capillary wall, thus forming the optically accessible sample chamber. A cryogen delivery line is operatively connected to the capillary encasement at an inlet end, and an exit line is operatively connected to the capillary encasement at an outlet end. A stress relief means is provided proximal to the inlet end of the capillary encasement for reducing turbulence of a cryogen entering the capillary encasement.

The invention further provides a method for performing capillary electrophoresis of a sample containing a fluorescent target species comprising:

(a) providing a capillary cryostat comprising:
  (i) a capillary comprising a transparent annular wall; and
  (ii) a capillary encasement comprising a transparent portion, wherein at least a portion of the transparent annular wall of said capillary is surrounded by the transparent portion of the capillary encasement to form an optically accessible sample chamber; said capillary encasement further comprising a transparent annular wall forming a lumen surrounding the portion of the transparent annular wall of said capillary that is surrounded by the transparent portion of the capillary encasement;
(b) electrophoresing the sample through the capillary to position the target species in the optically accessible sample chamber;
(c) freezing the target species by introducing a cryogen into the lumen of the capillary encasement;
(d) irradiating the frozen target species to induce fluorescence emission from target species; and
(e) detecting the fluorescence emission.

The method can be used to obtain non-line narrowing (NLN) spectra (preferably at 77K using liquid nitrogen as the cryogen) and fluorescence line narrowing (FLN) spectra preferably at 4.2K using liquid helium as the cryogen). These spectra can be analyzed by comparing the resulting high resolution FLN fingerprint spectra of a target species with available libraries containing FLN spectra of standard compounds to obtain structural information about the separated analytes.

The present invention permits on-line, high resolution fluorescence spectroscopy of electrophoretically separated analytes by allowing low temperature excitation and detection. Immobilization of the electrophoretically separated analytes, by freezing, allows spectroscopic interrogation for essentially unlimited periods of time. On-line structural characterization of closely related analytes using fluorescence line-narrowing spectroscopy (FLNS) can thereby be achieved.

BRIEF DESCRIPTION OF THE DRAWINGS

FIG. 2 is a schematic diagram of a capillary cryostat.

DETAILED DESCRIPTION OF THE INVENTION

Figure 1:
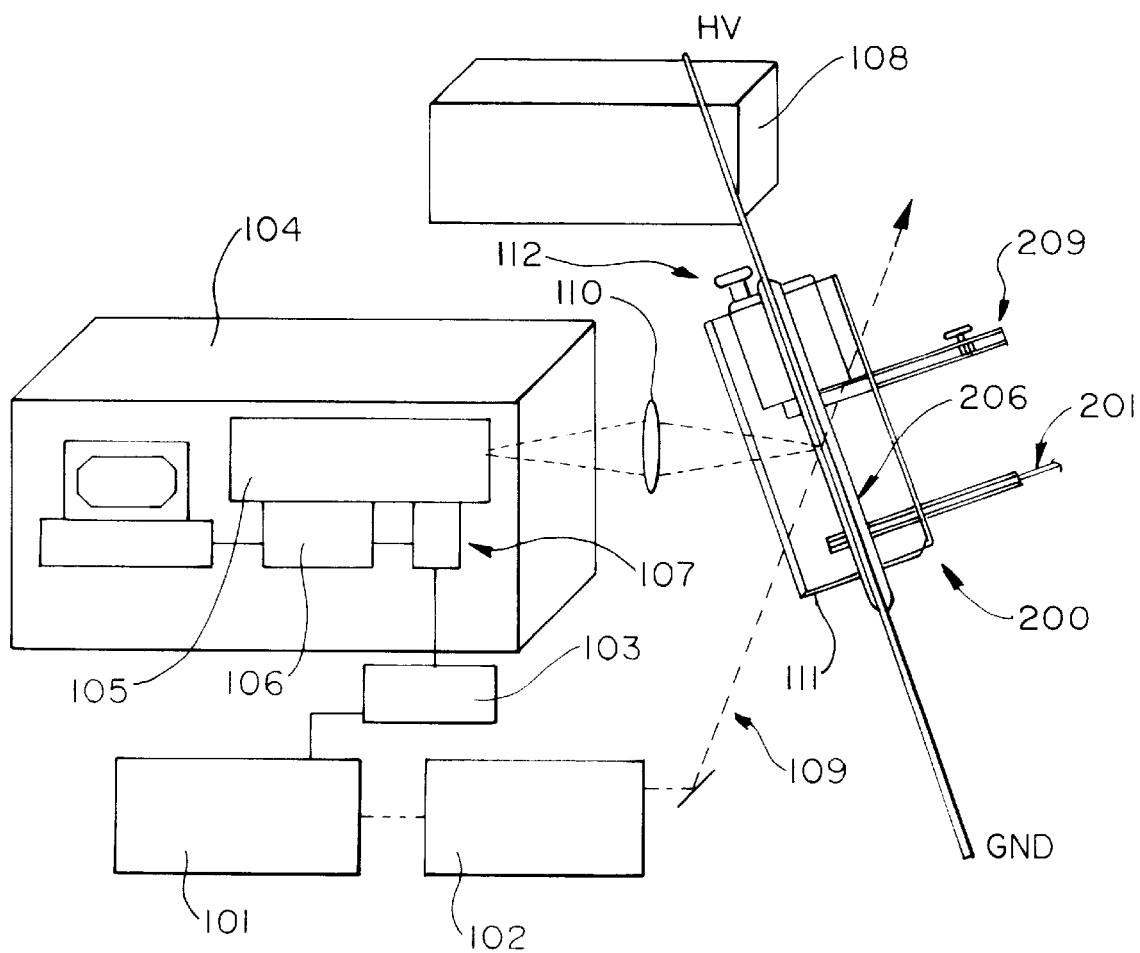
FIG. 1 is a schematic diagram of a CE-FLN system used for structural characterization of molecular analytes; HV, high voltage; GND, ground.

Fluorescence line-narrowing spectroscopy (FLNS) is a simple and practical analytical methodology. In recent years, the prowess of FLNS has been convincingly demonstrated by in vitro and in vivo studies of DNA damage from carcinogenic PAH such as benzo[a]pyrene, 7,12-dimethylbenz[a]anthracene, and the most potent PAH carcinogen currently known, dibenzo[a,l]pyrene. FLNS is capable of distinguishing between a given PAH metabolite covalently bound to different DNA bases (R. Jankowiak et al., *Chem. Res. Toxicol.* 1991, 4, 256–269; R. Jankowiak, et al., *Chem. Res. Toxicol.* 1988, 1, 60–68) and to different nucleophilic centers of a given base (K-M. Li et al., *Biochemistry* 1995, 34, 8043–8049; P. D. Devanesan et al., *Chem. Res. Toxicol.* 1993, 6, 364–371). FLNS has even been used to distinguish between a given metabolite bound in helix-external, partially base-stacked, and intercalated conformations (R. Jankowiak, et al., *Chem. Res. Toxicol.* 1988, 1, 60–68; M. Suh et al., *Biophys. Chem.* 1995, 56, 281–296; M. Suh et al., *Carcinogenesis* 1995, 16, 2561–2569).

The present invention successfully interfaces fluorescence line-narrowing (FLN) spectroscopy with capillary electrophoresis (CE) so as to provide on-line structural characterization of electrophoretically separated, structurally similar molecular analytes. The CE-FLN apparatus of the invention allows low temperature, on-line fluorescence detection of CE-separated analytes under both non line-narrowing and line-narrowing conditions, making possible the production of both three-dimensional electropherograms and high resolution spectra at the temperature of liquid helium (about 4.2K). Low temperature measurements often result in higher quantum yields of many analytes, thus increasing the detection limits. Significantly improved overall resolution and structural characterization ("fingerprinting") of molecular analytes is thereby achieved, and analyte detection levels are typically in the sub-femtomole range.

The present invention provides a CE-FLN system (e.g., FIG. 1) comprising an capillary cryostat having an optically accessible low-temperature sample chamber, a spectrally narrow excitation source, and a wavelength-dispersive detection system. The capillary cyrostat (e.g., FIG. 2) includes a capillary having a transparent annular wall that forms an interior portion suitable for placement of a target species, and a capillary encasement at least a portion of which is transparent. The transparent portion of the capillary encasement surrounds at least a portion of the transparent annular capillary wall to form the optically accessible sample chamber.

The spectrally narrow excitation source is positioned to direct a beam of light into the interior portion of the capillary to induce fluorescence emission from a target species. Preferably, the excitation beam passes through the transparent portion of the capillary encasement prior to contacting the target species. The wavelength-dispersive detection system is positioned to detect the fluorescence emission from the target species, and is preferably positioned to detect the target species emission through the transparent portion of the capillary encasement.

In a preferred embodiment, the capillary cryostat is mounted on a translational stage capable of moving the sample chamber along a capillary axis, relative to the excitation source. Optionally, the system can include additional elements of a modular CE system such as a high voltage power supply, automated sample introduction and flow control system, and additional UV absorption or fluorescence detectors to monitor the migration rates of the analytes.

The term "optically accessible" means transparent to light, preferably light having wavelengths about equal to the wavelengths of the excitation source and the analyte emission. Transparency to light having a wavelength of about 200–1000 nm is preferred, more preferably about 250–850 nm. The term "low-temperature" means a temperature below 100K., preferably about 2K.–90K., more preferably about 4K.–80K.

The apparatus of the invention can be used in either capillary zone electrophoresis (CZE) or capillary gel electrophoresis (CGE). When the apparatus is in use, the capillary preferably contains an eluant that, when frozen, is transparent to light; i.e., that forms a disordered matrix upon freezing. The choice of eluant is dependent on the application, and the eluant can comprise an organic or aqueous buffer, preferably an aqueous buffer comprising a salt. Alternatively, the eluant can comprise a gel (such as a polyacrylamide), or any other matrix suitable for use in capillary electrophoresis that forms a disordered matrix upon freezing.

Capillaries

That portion of the capillary that forms part of the sample chamber is optically accessible, as described above. Preferably, the capillary is fabricated from UV-transparent fused silica capillary tubing. The optimum internal diameter of the capillary depends on the application or experiment: larger diameters produce stronger signals because they allow interrogation of a greater amount of analyte, but narrow diameters are generally associated with higher resolution electrophoretic separations. Typically the internal diameter of the capillary ranges from 50–100 µm, although it is to be understood that any internal diameter suitable for capillary electrophoresis is suitable for the capillary present as part of the sample chamber, provided it fits within the capillary encasement.

The present invention is not limited by the length of the capillary; the capillary need only be sufficiently long to effectuate the desired electrophoretic separation and accomodate the capillary cyrostat. Preferably, the capillary is 50–100 cm in length, more preferably 60–80 cm in length.

The section of the capillary to be cooled (i.e., that section that forms part of the sample chamber) has a low thermal capacity, ensuring rapid freezing of the capillary contents when the cryogen is introduced. This ensures rapid freezing of the capillary contents when the capillary cryostat is filled with a cryogenic fluid, producing immobilized "plugs" containing separated analytes ready for further interrogation. Rapid freezing is advantageous because it minimizes analyte band dispersion within the capillary.

Capillary Cryostat (CC)

Referring now to FIG. 2, a capillary cryostat 200 according to the invention is shown. A cryogen enters the capillary cryostat 200 through an entry port 201 from a cryogen storage container and cryogen feed line (both not shown). The cryogen is preferably liquid nitrogen or liquid helium (or the cold vapors from these liquids present immediately above the liquid surface). It is preferred that entry port 201 includes a gas seal 201a to prevent the cryogen from escape during operation. Typically, the gas seal 201a can be made of any material capable of sealing at room temperature. Suitable seals may be O-rings, for example, VITON available from dupont De Nemours, Wilimington, Del., or BUNA-N, available from Parker Seals, Lexington, Ken. The cryogen passes through a delivery line 202 that preferably includes co-axial members, in particular, an outer vacuum wall 202a and an inner vacuum wall 202b. An outer diameter of the delivery line 202 is preferably about 2–3 cm and the delivery line 202 is preferably about 40–50 cm in length. An insulating vacuum is preferably formed between the outer vacuum wall 202a and the inner vacuum wall 202b. The insulating vacuum separates these co-axial members. This is a desirable feature because, in general, external members, such as the outer vacuum wall 202a, remain at ambient temperature during operation of the capillary cryostat and heat is not conducted to the cryogen. Internal members, thus, such as the inner vacuum wall 202b, experience temperature changes from ambient temperature to selected low temperatures upon exposure to the cryogen.

A cryogen feed line (not shown) is preferably detachable from the capillary cryostat by an O-ring compression fitting 201 that is in close proximity to a taper seal 203, when the capillary cryostat is fully assembled. The compression fitting 201 serves to keep the cryogen feed line seated in place so that escape of the cryogen is prevented. A stagnant gas column in the delivery line 202 provides an effective means of thermal protection from the compression fitting. If the cryogen were to escape at this junction, the compression fitting would eventually cool to the extent as to become ineffective. An ineffective compression fitting would likely decrease the efficiency of the capillary cryostat by allowing cryogen to escape. An effective compression fitting decreases the likelihood of introducing cryogen turbulence because of an improperly positioned delivery line. The taper seal 203 is preferably in proximity to an inlet portion of a capillary encasement 206. It is preferable to reduce turbulence in cryogen flow to maximize capillary cryostat efficiency.

It is important that the cryostat retain structural integrity when the internal members are subjected to the selected low temperatures. Stress relief means are provided in the capillary cryostat. One preferable means includes a stress relief conduit 204 that has a shape capable of accommodating size changes during thermal contraction, while maintaining a cross-sectional area in the delivery line 202, upon cryogen entrance. One preferred configuration is a coil shape, as shown. Preferred dimensions of a suitable coil configuration include an outer diameter of about 2–3 mm, a wall thickness of about 0.25 mm of a 305 SS tubing. In particular, the stress relief conduit 204 provides axial compensation for the change in length of the internal components relative to the outer components, due to the respective temperature exposures as described above. The compensation alleviates the predicted perpendicular strains that may be imposed on a capillary encasement 206, described below.

Figure 2A:
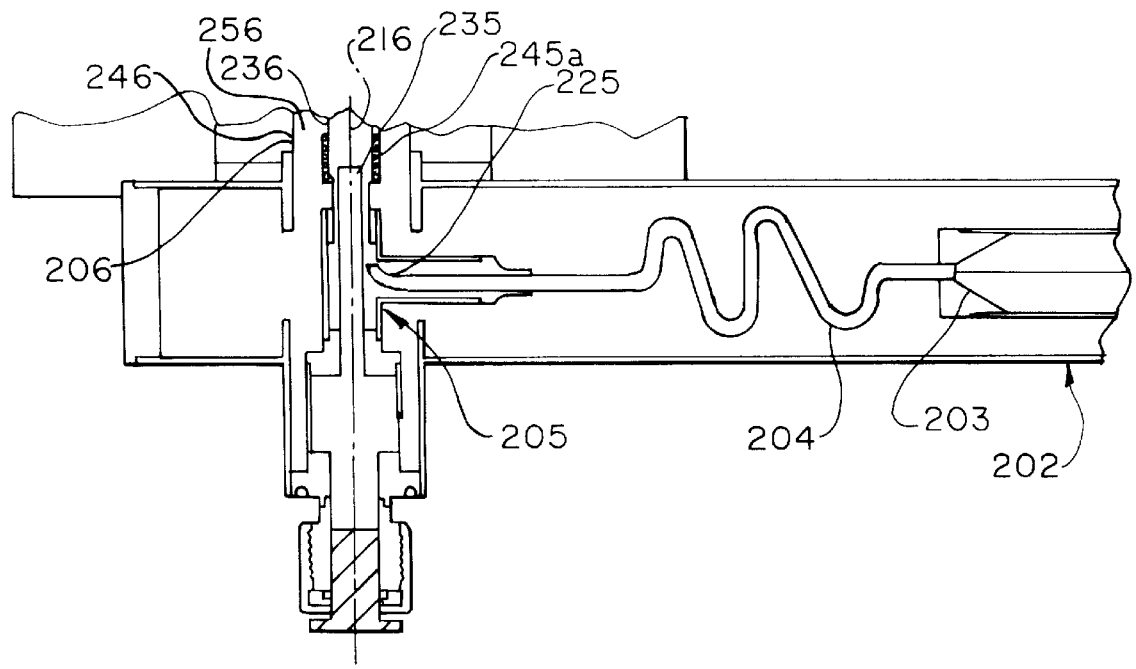
FIG. 2A is a schematic enlargement of an inlet portion of a capillary cryostat.

In order to minimize internal thermal stress, i.e., contraction, of the capillary, the cryogen passes from the stress relief conduit 204 through a cryogen entry segment 205. Referring now to FIG. 2A, an enlarged view of a portion of the capillary cryostat around the entry segment 205 is shown. As the cryogen passes from the stress relief conduit 204, it first passes through a diverter portion 225 of the entry segment 205. Preferably, the diverter portion 225 is configured such that the cryogen is aimed in a direction substantially normal (i.e., perpendicular) to the prior path of the cryogen in the delivery line 202 and that is substantially parallel to a longitudinal axial direction of the capillary 216. That is, the diverter portion 225 directs the cryogen such that it flows along the length of the capillary 216. The cryogen then passes around a turbulence guard 235 that functions to prevent buffeting from the cryogen. Preferably, the turbulence guard 235 surrounds at least a portion the capillary 216 for improved protection from turbulence.

Prior to contacting a capillary 216, the cryogen passes around a cold tube seal 245a. It is preferred that the cold tube seal 245 be formed from a material that exhibits a similar coefficient of thermal expansion as a capillary encasement 206, described below. For example, when the capillary encasement 206 is formed from quartz, a particularly useful material for the cold tube seal 245a is INVAR, available from Scientific Alloys, Westerly, R.I. Preferably, the cold tube seal 245a is sealed to an inner annular wall 236 of the capillary encasement 206 with a sealant capable of withstanding the cool operating temperatures. An outer annular wall 246 is preferably sealed in a tube-in-socket configuration using an epoxy sealant. An example of a suitable epoxy sealant is STYCAST 2850FT/24LV, available from Emerson & Cuming, Lexington, Mass. Additionally, to improve the seal between the cold tube seal 245a and the capillary encasement 206, the relevant portion of the capillary encasement 206 can be etched with hydrofluoric acid to improve epoxy adhesion thereto.

As shown in FIG. 2A, the cryogen entry segment 205 directs the cryogen to flow in a direction substantially normal to the flow between the entry port 201 and a downstream end of the stress relief conduit 204. As shown in FIG. 2A, cryogen flow is directed by the diverter portion 225. It is believed that this feature functions to prevent damage and decrease the likelihood of breakage of the capillary upon contact with the cryogen.

Referring back to FIG. 2, the capillary 216 is housed in a capillary encasement 206. Preferably, the capillary encasement 206 includes an inlet end in proximity to the cryogen entry segment 205 and an opposing outlet end. The inlet end provides the introduction of the cryogen to the capillary encasement 206 while the outlet end provides the evacuation of the cryogen from the capillary encasement 206. The capillary encasement 206 preferably includes an inner annular wall 236 and an outer annular wall 246 forming an annular lumen 256 therebetween. Preferably, the annular lumen 256 is evacuated to provide a thermal barrier. Suitable dimensions for a capillary encasement 206 are about 0.5–0.8 cm in diameter and about 6–9 cm in length. The capillary 216 is located co-axially within the capillary encasement 206 and positioned with terminal components of the capillary encasement 206, discussed below. When used in a CE-FLN system in according to the invention, the capillary 216 is preferably positioned in a central transparent region (not labeled) of the capillary encasement 206.

Preferably, the capillary 216 is cooled to a temperature of about 77K to about 4.2K by a continuous flow of cryogen through the capillary encasement 206. For example, liquid nitrogen may be used for NLN fluorescence and liquid helium may be used for FLNS. The low thermal capacity of the capillary 216 and the small dimensions of the capillary encasement 206 ensure rapid cooling in preferably about 1 minute or less. It will be appreciated that cooling must be rapid in order to produce disordered matrices as required.

Figure 2B:
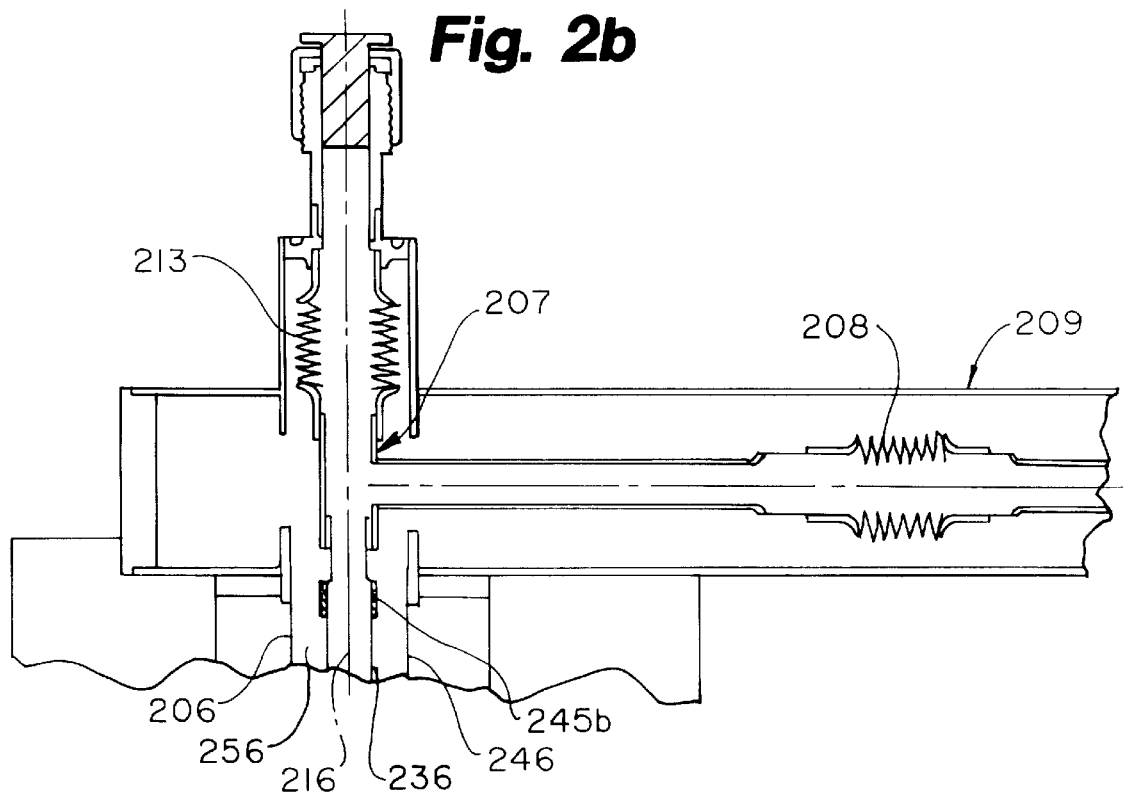
FIG. 2B is a schematic enlargement of an outlet portion of a capillary cryostat.

At the outlet end of the capillary encasement 206, a cryogen exhaust segment 207 is provided. Referring now to FIG. 2B, the cryogen exhaust segment 207 is preferably substantially similar in configuration as the cryogen entry segment 205. The exiting cryogen passes around a cold tube seal 245b. It is preferred that the cold tube seal 245b be formed from a material that exhibits a similar coefficient of thermal expansion as a capillary encasement 206. For example, when the capillary encasement 206 is formed from quartz, a particularly useful material for the cold tube seal 245b is INVAR, available from Scientific Alloys, Westerly, R.I. Preferably, the cold tube seal 245b is sealed to an inner annular wall 236 of the capillary encasement 206 with a sealant capable of withstanding the cool operating temperatures. An outer annular wall 246 is preferably sealed in a tube-in-socket configuration using an epoxy sealant. An example of a suitable epoxy sealant is STYCAST 2850FT/24LV, available from Emerson & Cuming, Lexington, Mass. Additionally, to improve the seal between the cold tube seal 245b and the capillary encasement 206, the relevant portion of the capillary encasement 206 can be etched with hydrofluoric acid to improve epoxy adhesion thereto.

Upon exiting the cryogen exhaust segment 207, the cryogen is now flowing in a direction substantially normal to the orientation of the capillary 216 and substantially parallel to the direction of the delivery line 202 but through an exit line 209. Again, to minimize potential stress upon cooling and warming the capillary 216 during operation of the capillary cryostat, a thermal contraction bellow 208 is provided in an upstream end of an exit line 209, thus connecting the cryogen exhaust segment 207 to the exit line 209. An axial stress relief bellow 213 is also provided and is preferably oriented in a direction substantially parallel to, and preferably in fluid communication with, the capillary 216. Both bellows (208 and 213), together, provide an extended thermal path from the cool area within and to the ambient temperature portion of the capillary encasement 206. This minimizes the likelihood for the accumulation of condensation on the capillary cryostat. Additionally, any axial contraction upon cooling and subsequent expansion upon warming of the capillary 216 is accommodated by the axial stress relief segment 213.

As described with respect to delivery line 202, exit line 209 preferably includes an outer vacuum wall 209a and an inner vacuum wall 209b. An outer diameter of the exit line 209 is preferably about 2.54 cm (1.0 in) and is preferably about 44.5 cm in length. An evacuation valve 210 is preferably operatively connected to exit line 209. The evacuation valve 210 can be opened to facilitate evacuation of the insulating vacuum, as desired. Subsequent warning may be achieved by replacing the cryogen with nitrogen or helium gas tempered as required. The cryogen then exits the capillary cryostat 200 by flowing through exit port 211, that may either be connected for reclamation, recycling or disposing of the cryogen.

Sealing of the capillary 216 is accomplished by warm gas seals 214a and 214b that are provided in proximity to the inlet end and the outlet end of the capillary encasement, respectively. These warm gas seals are preferably Teflon and are modified to allow threading of the capillary 216. These warm gas seals provide both electrical and thermal isolation for the capillary. These warm gas seals may also include compression O-rings, wherein escape of the cryogen is prevented by filling an annulus about the capillary 216 and an inner surface of warm gas seals 214a and 214b with a standard vacuum grease. The grease is preferably viscous enough to prevent blowing out during initial cool down and should freeze in place during operation.

To provide additional support for the capillary encasement 206, "L-brackets" 212a and 212b are provided, wherein the capillary encasement 206 cannot torque upon cooling and subsequent warming, presumably due to, at least in part, the excess weight of the cryogen feed line (not shown), exit line, vacuum pumping hoses (not shown), and exhaust or reclamation adapters (also not shown). Preferably, these L-brackets are adapted to ride on the translator (not shown). Thus, these L-brackets provided both support to the capillary encasement and an attachment means of the capillary cryostat to the translator.

If desired, the temperature in the interior portion of the capillary can be varied or controlled by adjusting the flow rate of the cryogenic fluid. Optionally, the crystostat can include a temperature monitor positioned directly opposite the ventline.

At the low temperature provided by the crystostat, the contents of the encapsulated portion of the capillary freeze, rendering the separated analytes present therein immobile. FLNS and/or NLN fluorescence spectroscopy can then be conducted on the stationary analytes for arbitrary detection times, significantly improving both the accuracy of quantitation and the limit of detection.

As a component of the FLN-CE apparatus of the present invention, the crystostat is preferably attached to a translation stage, more preferably a stage with an automated controller. Finely controlled translation of the crystostat along the longitudinal capillary axis allows the separated analytes to be sequentially characterized by fluorescence spectroscopy, as the capillary is translated through the laser excitation region. The length of the crystostat, and its quartz cell, may at times be greater than the travel distance of the translation stage (typically about 5 cm); if the travel distance of the automated translation is insufficient, the frozen capillary can be manually positioned to a new location.

As an element of the CE-FLN system of the invention, the long axis of the crystostat (i.e., the capillary axis) is tilted relative to the excitation source, preferably about 30 degrees or less, to discriminate against scattered and reflected laser light. Further discrimination against scattered laser light and background fluorescence from the capillary walls was obtained by spatial filtering.

Excitation Source

The spectrally narrow excitation source preferably emits a beam of light having a range of wavelengths of less than about one wavenumber. A preferred spectrally narrow excitation source is a laser, more preferably a tunable laser. The laser used reflects the excitation wavelength needed to excite the analyte of interest. The laser can be either a continuous wave (CW) laser or a pulsed laser. A nonexpressive diode can also be easily included in the CE-FLN system. An excimer pumped-dye laser is particularly preferred. For example, an excimer (XeCl gas) pumped dye laser can be used for analysis of analytes that absorb in the 330–900 mn region; other gases, such as Kr, can be used for analysis of analytes that absorb in the 310–1000 nm range. The average power density of the laser preferably ranges from 1–100 mW/cm$^2$.

Wavelength-Dispersive Detection System

The wavelength-dispersive detection system comprises a fluorescence dispersive device, such as a high resolution monochromator, and a detector. The detector is preferably a diode array detector or an image array detector. The image array detector is preferably a two-dimensional image array detector, more preferably a charge-coupled device (CCD) or a charge-injection device (CID). In a particularly preferred embodiment, an optical multianalyzer (OMA) is included in the wavelength-dispersive detection system. Preferably, fluorescence is collected by the detector at a right angle with respect to the excitation beam.

One-dimensional (total signal) electropherograms can be obtained either by integrating the NLN spectra obtained at 77K, or by direct measurement of total fluorescence intensity at higher, including ambient, temperatures. The present apparatus thus optionally includes a second fluorescence-based detector for acquiring room temperature chromatograms. The second detector can, for example, be a photomultiplier tube or a fast-response diode.

CE Apparatus

It is to be understood that the FLNS-CE interfacing accomplished by the present invention is generally applicable to any modular CE apparatus or system, and that any and all such systems can be utilized as a component of the apparatus of the present invention provided that the capillaries used in such system can withstand the local low temperature environment of the capillary cryostat and are fabricated from a material that allows effective on-line excitation and detection of the separated analytes.

A preferred embodiment of the CE-FLN system of the invention is shown in FIG. 1. The apparatus includes a tunable excitation source consisting of an excimer laser 101, a dye laser 102, and a pulser 103, a spectrometer 104 housing a high resolution monochromator 105 and an optical multianalyzer (OMA) 106 with an intensified diode array detector 107, a capillary cryostat 200, and modular CE apparatus 108. As previously mentioned, the capillary cryostat includes a capillary encasement 206 surrounding the capillary 216. The laser 101, 102 is positioned to direct a beam 109 of spectrally narrow light so as to irradiate a frozen analyte inside a sample chamber formed by transparent portions of capillary 216 and encasement 206. Fluorescence emitted by the frozen analyte passes through a lens 110 and is detected by the spectrometer 104. The cryostat 200 is attached to a translational stage 111 that is operated by a translator motor 112.

The present invention also provides a method for performing capillary electrophoresis utilizing the apparatus of the invention disclosed herein. Preferably, the capillary is first filled with an eluant capable of forming a disordered matrix upon freezing, as described above. The method is performed by electrophoresing a sample containing a fluorescent target species through a capillary to position the target species in the optically accessible sample chamber of the capillary cryostat. At that point the capillary is rapidly cooled to a low temperature by introducing a cryogen, preferably a cryogenic liquid, into the inner lumen of the capillary encasement, thus freezing the contents of the encapsulated portion of the capillary, including the target species. The frozen target species is irradiated, preferably with a CW or pulsed laser, and the induced fluorescence emission in CW or gated mode is detected.

Optionally, the detection step includes the acquisition of non-line-narrowed (NLN) fluorescence spectra, preferably using liquid nitrogen (77K) as the cryogen, to obtain information concerning the position (wavelength) of the fluorescence (0,0) band and the vibronic band structure of CE-separated analytes. Knowledge of the fluorescence origin band position (from the NLN spectra) is helpful in selecting the appropriate laser excitation wavelengths for subsequent FLN characterization of the analyte. Acquisition of high resolution spectra using FLNS, preferably using liquid helium as the cryogen (4.2K), preferably follows. In a preferred embodiment of the method, FLN spectra are obtained for several excitation wavelengths (preferably 6–8 wavelengths) to obtain all excited state vibrational frequencies. When multiple wavelengths are used, each excitation wavelength provides a unique fingerprint. Structural characterization is obtained by a comparison of these spectra with available libraries of FLN spectra of standards.

The present invention is well-suited for distinguishing components of complex systems, as is demonstrated by the following examples. Other examples for use of the FLN-CE apparatus of the invention include rapid detection and high resolution structural identification of the chemical compounds formed in the reaction of cellular macromolecules with the electrophilic metabolites of aromatic hydrocarbons and related chemicals. Many other important applications can be envisioned, such as the study of the relationship between adduct conformation and stereochemistry, studies of the effect of the flanking bases on the adduct structure of DNA hotspots, and analysis of isomers and other closely related compounds. Due to the sub-femtomole detection level of the present invention, many challenging problems in biological, medical, and forensic sciences can be addressed. There is, for example, mounting evidence that depurinating adducts may be responsible for tumor initiation. The present invention can be used to characterize depurinating nucleoside adducts in urine and/or supernatant form cell ensembles in vitro and in vivo. Thus, use of the present invention in broad screening applications to detect depurinating DNA adducts may prove to be very important for cancer treatment and prevention.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLE I

Analyis of Polyaromatic Hydrocarbons (PAH) Using FLN-CE Capillary Electrophoresis System A Crystal 300 Series modular CE system (model 310, ATI Unicam, Boston, Mass.) was used for electrophoretic separations. Absorption electropherograms were recorded using an ATI Unicam model 4880 Chromatography Data Handling system, with detection at 254 nm. UV-transparent fused silica capillary tubing (Polymicro Technologies, Phoenix, Ariz.) was 75 $\mu$m ID. For the CE-LIF experiments, a 95 cm long capillary was used, with the absorbance detector positioned 40 cm from the capillary inlet and the capillary cryostat (CC) approximately 85 cm from the inlet. For this arrangement, analyte peaks are less well resolved in absorbance than fluorescence, simply because the absorbance detector is located upstream from the CC.

A mixture of five PAH was selected as the sample to be used in the initial CE-FLN experiments. The scheme of Shi and Fritz [Y. Shi et al., Anal. Chem. 1995, 67, 3023–3027; Y. Shi et al, J. High Res. Chrom. 1994, 117, 713] was used for CE separation. The buffer consisted of an acetonitrile-water solution (30% v/v) containing 40 mM sodium di-2-ethylhexyl sulfosuccinate (Aldrich, Milwaukee, Wis.) and 8 mM sodium borate (Fisher Scientific, Fair Lawn, N.J.), adjusted to pH 9 by adding phosphoric acid (Fisher Scientific). The capillary was initially conditioned by rinsing it with 0.1M NaOH for 30 minutes, deionized water for 30 minutes, and running buffer for 5 minutes. Hydrodynamic injection of the 5-PAH mixture—50 ppm each of 1-hydroxypyrene, pyrene, benz[a]anthracene (B[a]A), benzo[e]pyrene (B[e]P), and benzo[a]pyrene (B[a]P)—at 20 mbar for 3 seconds was used. The calculated injection volume was approximately 8 nL, corresponding to an absolute amount of 400 pg for each PAH, well above the FLNS detection limit. Separation was performed at an applied voltage of 25 kV. When the voltage was turned off, the capillary was cooled to low temperature for laser-excited fluorescence experiments.

Low Temperature Fluorescence Apparatus

The instrumentation used for low temperature laser-excited fluorescence spectroscopy was as described in [R. Jankowiak et al., *Chem. Res. Toxicol.* 1991, 4, 256–269]. Briefly, the excitation source was a Lambda Physik (Acton, Mass.) Lextra XeCl excimer laser—FL-2002 dye laser system. CE-separated analytes were probed with the excimer laser under non-line-narrowing (NLN) conditions (77K, 308 nm excitation) or with the dye laser under line-narrowing (FLN) conditions (4.2K, $S_1 \leftarrow S_0$ excitation). Fluorescence was collected at a right angle to the laser excitation beam and dispersed by a McPherson (Acton, Mass.) model 2061 1-m monochromator. For NLN measurements, a resolution of 1.3 nm (150 G/mm grating and 200 $\mu$m entrance slit) was used, providing a spectral window of approximately 160 nm for a Princeton Instruments (Trenton, N.J.) IRY-1024/GRB intensified diode array detector. For FLN spectra, a resolution of 0.08 nm (2400 G/mm grating and 200 $\mu$m slit) was used, providing an about 10 nm window. The diode array was operated in a gated detection mode, using the output of a reference photodiode to trigger a Princeton Instruments FG-100 high voltage pulse generator. The spectra presented here were acquired using a 40 ns delay and a 200 ns gate width; the laser repetition rate was 10 Hz.

Interfacing CE with FLN Spectroscopy

The CE-FLN system incorporated the modular CE system, the FLN apparatus, and a capillary cryostat (CC). The CC was formed from a double-walled quartz cell with inlet and return lines for introducing liquid nitrogen or liquid helium. The outer portion of the CC was evacuated. The capillary, positioned in the central region of the CC, was cooled to 77K by a continuous flow of liquid nitrogen through the cryostat (for NLN fluorescence) or to 4.2K using liquid helium (for FLNS). The low thermal capacity of the capillary section to be cooled and the small dimensions of the CC (inner portion, 4 mm ID×22 cm length) ensured rapid cooling. Warming was achieved by closing the coolant flow regulator or by replacing the cryogenic liquid with nitrogen or helium gas.

The CC was attached to a translation stage (model TM-200-SM and model 201 controller, New England Affiliated Technologies, Lawrence, Mass.). Translation of the CC and capillary in the direction of the capillary axis allowed the separated analytes to be sequentially characterized by fluorescence spectroscopy, as the capillary is translated through the laser excitation region. The length of the CC (22 cm) and its quartz cell (7 cm optical window) were greater than the travel distance of the translation stage (5 cm); if the 5 cm automated translation proved insufficient, the frozen capillary was manually positioned to a new location. Fluorescence is collected at right angle with respect to the excitation laser beam. To discriminate against scattered and reflected laser light, the CC was tilted by 20°. Further discrimination against scattered laser light and background fluorescence from the capillary walls was obtained by spatial filtering.

Fluorescence of CE-separated analytes was detected first under NLN conditions at 77K using excimer laser excitation at 308 nm. NLN fluorescence spectra acquired during translation of the CC provided the basis for generation of fluorescence electropherograms from a plot of the integrated fluorescence intensity as a function of time (or capillary position). NLN provides low resolution but useful fluorescence spectral information for each of the separated analytes. After the electropherograms are generated, the temperature of the capillary was lowered to 4.2K for high resolution FLN characterization. Selective excitation using the excimer pumped dye laser provides FLN spectra for the analytes at various vibronic ($S_1 \leftarrow S_0$) excitation wavelengths. Each excitation wavelength provides a unique fingerprint. The use of low temperatures alleviates the problems with room temperature photodegradation of analytes. Spectral hole burning which is deleterious to FLN [R. Jankowiak et al., *Chem. Res. Toxicol.* 1991, 4, 256–269; R. Jankowiak et al., *Chem. Rev.* 1993, 93, 1471–1502], was found to be inefficient at 4.2K and absent above 30K.

Formation of Capillary Glasses

An important concern was whether the acetonitrile-water-based buffer with added DOSS would form the necessary disordered glassy matrix. Even if it did, there was a serious question whether its instability would lead to sudden and violent cracking which, in turn, would destroy the capillary. Neither acetonitrile or water by themselves form clear glasses under normal cooling conditions [J. D. Winefordner, et al., *Anal. Chem.* 1963, 35, 2211–2212]. In fact, for water the transition to the glassy state (glass transition temperature of 135K.) is frustrated by formation of hexagonal ice upon solidification. (This can be circumvented by hyperquenching at a rate of $10^6$–$10^7$ $Ks^{-1}$ [W-H. et al., *J Phys. Chem.* 1995, 99, 7300–7310].) Nevertheless, it was found that the buffer in the capillary consistently formed a glassy matrix. Possibly this response can be attributed to the presence of salts (buffer), which are known to assist in the formation of the glassy state [C. A. Angell et al., *Chem. Phys.* 1970, 52, 1058–1068], and/or the small internal diameter of the capillary combined with its very low thermal capacity, which allow for quite rapid cooling.

Figure 3:
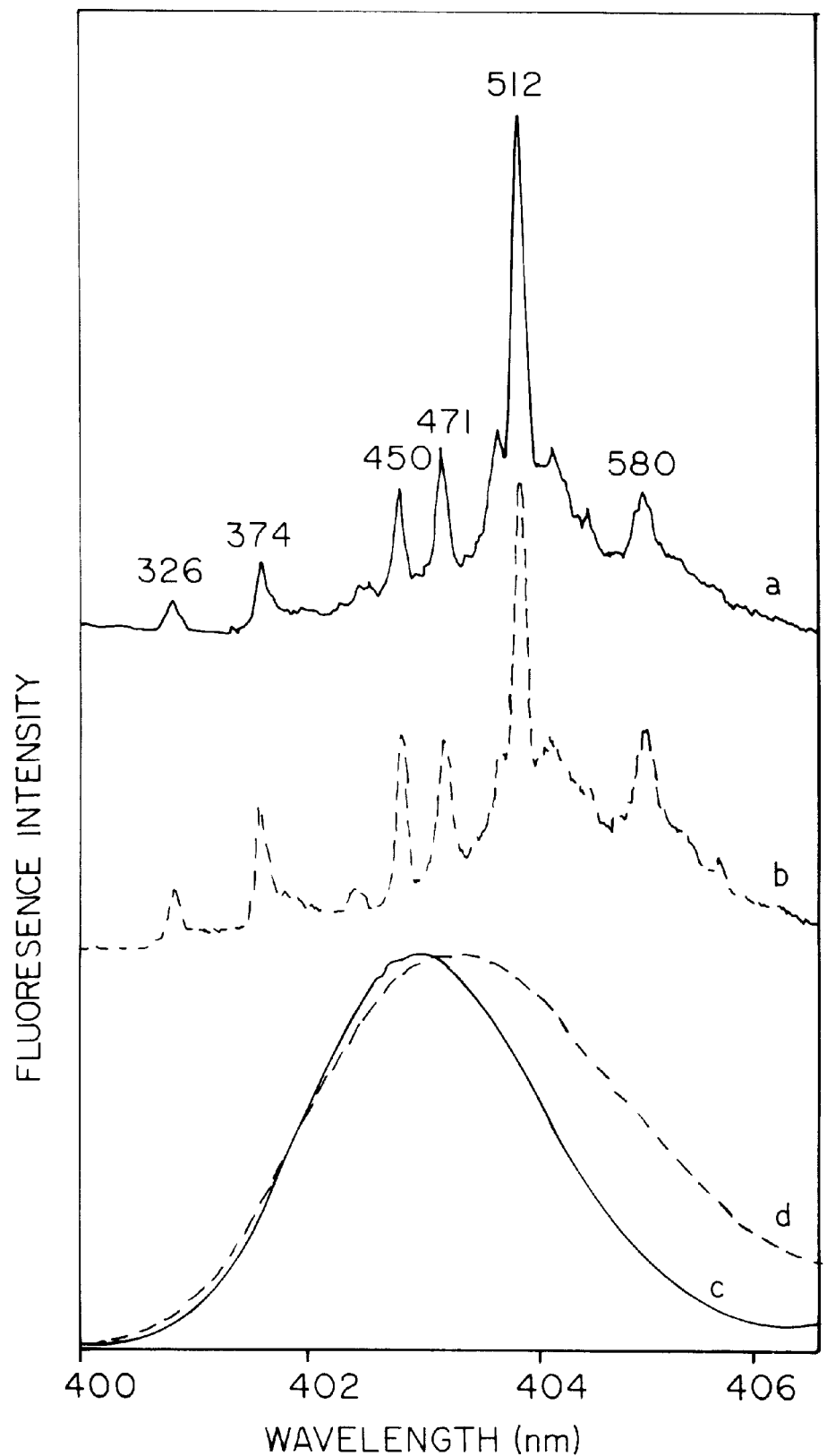
FIG. 3 depicts FLN spectra of B[a]P in (a) ethanol and (b) the CE buffer, obtained at 4.2K for an excitation wavelength of 395.7 nm. Modes are labeled with their excited state vibrational frequencies in $cm^{-1}$. NLN fluorescence origin bands of B[a] in ethanol and CE-buffer matrices are shown as spectra (c) and (d), respectively.

That the frozen buffer matrix is highly structurally disordered was confirmed by the NLN and FLN spectra. Profiles (c) and (d) of FIG. 3 represent the non-line-narrowed (77K) fluorescence origin bands of B[a]P in an ethanol glass and the buffer matrix, respectively. The origin band for the buffer is slightly red-shifted (0.3 nm) and significantly broader. The latter indicates that the structural heterogeneity experienced by B[a]P in the buffer matrix is more severe than in the ethanol glass. This was also found to be the case for the other PAH studied. Spectra (a) and (b) are 4.2K vibronically-excited FLN spectra of B[a]P obtained with an excitation wavelength of 395.7 nm in the ethanol glass and buffer matrix, respectively. The bands (zero-phonon lines) are labeled by their excited state ($S_1$) vibrational frequencies. Within experimental uncertainty, $\pm 2$ $cm^{-1}$, they are identical for both hosts. The slight difference in the vibronic intensity distributions is the result of the larger inhomogeneous broadening for the buffer matrix and the small displacement between the fluorescence origin bands, spectra (c) and (d).

CE-FLN (NLN) Analysis of a Polyaromatic Hydrocarbon (PAH) Mixture

Figure 4A:
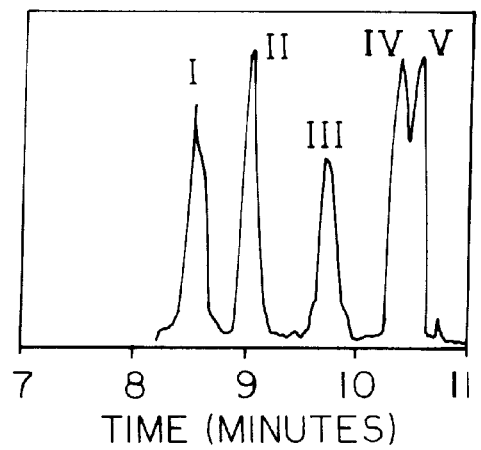
FIG. 4 depicts a three-dimensional plot of NLN fluorescence spectra obtained by translating the capillary through the laser excitation and fluorescence observation region for 1-hydroxyprene (I) and pyrene (II). Laser excitation wavelength 308 nm, T=77K, translation speed 0.65 mm/sec. Each trace represents a 1 second integrated fluorescence signal. Fluorescence (0,0) origin bands are indicated. Shown in the inset is the fluorescence electropherogram for the 5-PAH mixture, generated from the three-dimensional plots of NLN fluorescence vs. capillary position. Buffer, 40 mM sodium dioctyl sulfrosuccinate, 8 mM sodium borate, 30% (v/v) acetonitrile in water, pH 9; capillary length, 95 cm; applied voltage, 25 kV; current, 60 $\mu$A. The labeled peaks are 1-hydroxyprene (1), pyrene (II), B[a]A (III), B[e]P (IV), and B[a]P (V).
Figure 4B:
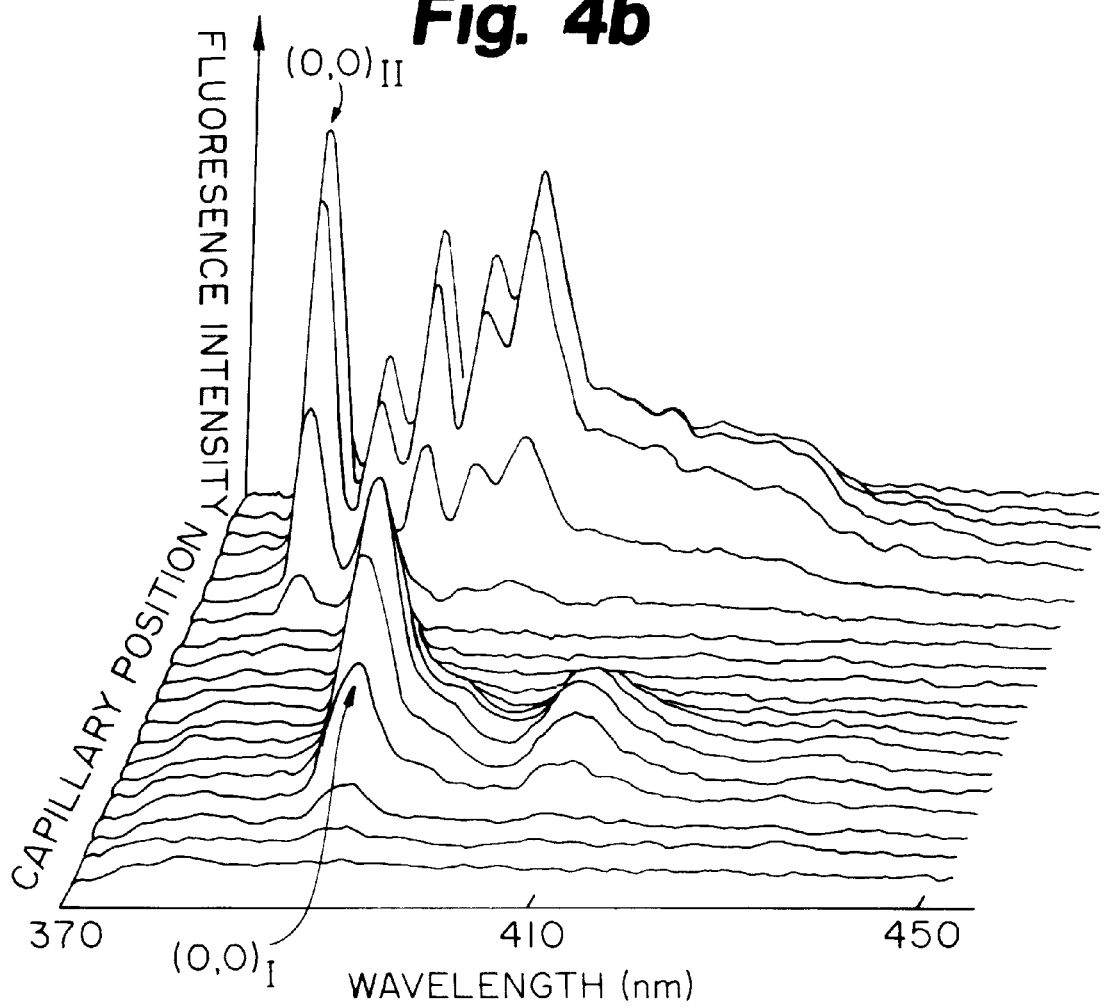

Absorbance electropherograms acquired for the separation of 1-hydroxypyrene, pyrene, B[a]A, B[e]P, and B[a]P indicated that the five PAH's could be resolved using the CE protocol described above. NLN fluorescence spectra acquired for CE-separated 1-hydroxypyrene (I) and pyrene (II) are shown in FIG. 4, as a three-dimensional plot of fluorescence intensity, wavelength, and capillary position. The average size of an analyte plug was about 3 mm. Each trace in FIG. 4 represents a 1 second fluorescence signal integration, as the capillary is translated through the laser excitation (308 nm excimer laser) and fluorescence observation region. For clarity, only the NLN spectra for 1-hydroxypyrene and pyrene have been shown in FIG. 4.

The NLN spectra provide low resolution spectral information for each of the analytes. The position of the (0,0) fluorescence origin band for these five PAH is different:

1-hydroxypyrene, 386 nm; pyrene, 372 nm; B[a]A, 385 nm; B[e]P, 376 nm; and B[a]P, 403 nm; this provides some degree of spectral resolution and identification. The relative intensity distribution of the vibronic bands for these PAH also vary, as shown in FIG. 4. 1-Hydroxypyrene has a relatively simple fluorescence spectrum compared to pyrene, which has many active, intense vibronic modes. The spectra shown in FIG. 4 illustrate the advantage of a wavelength dispersive detection system (monochromator with diode array) compared to fixed wavelength detection (filter-based or single-wavelength monochromator systems), for qualitative identification of analytes.

The inset of FIG. 4 is a fluorescence electropherogram generated from three-dimensional NLN spectra acquired for the CE-separated PAH mixture. The first part of the electropherogram (peaks I and II) corresponds to fluorescence at 385 nm shown in the spectra of FIG. 4. This is the (0,0) origin band of 1-hydroxypyrene, but a peak for pyrene is also seen in the electropherogram because of vibronic band fluorescence for pyrene at 385 nm. The remaining part of the electropherogram, obtained from NLN spectra not shown, corresponds to fluorescence at 385 nm for B[a]A (peak III) and B[e]P (peak IV) and at 403 nm for B[a]P (peak V).

The features of the fluorescence electropherogram are similar to those observed in absorbance. However, the electropherograms are not directly comparable because the detectors are located at different positions; the distance from the capillary inlet to the UV absorbance detector is 40 cm, while the distance to the CC is approximately 85 cm. The relative intensities in the electropherograms vary because of differences in absorption strengths compared to fluorescence quantum yields. In addition, the relative intensities of peaks in fluorescence electropherograms generated in this manner depend on the wavelength region(s) used to create the electropherograms. Incorporation of a second fluorescence-based detector (for acquiring room temperature electropherograms) very close to the inlet of the CC or within the CC would eliminate the differences observed in the current room temperature (absorption) and low temperature (fluorescence) electropherograms.

It should be noted that a better separation than that shown in FIG. 4 can be achieved by optimizing the DOSS and acetonitrile concentrations, but is not necessarily required for the CE-FLN system. Analytes that are not resolved in the CE separation can be identified and distinguished spectroscopically by their NLN fluorescence and (most importantly) their FLN spectra.

Figure 5:
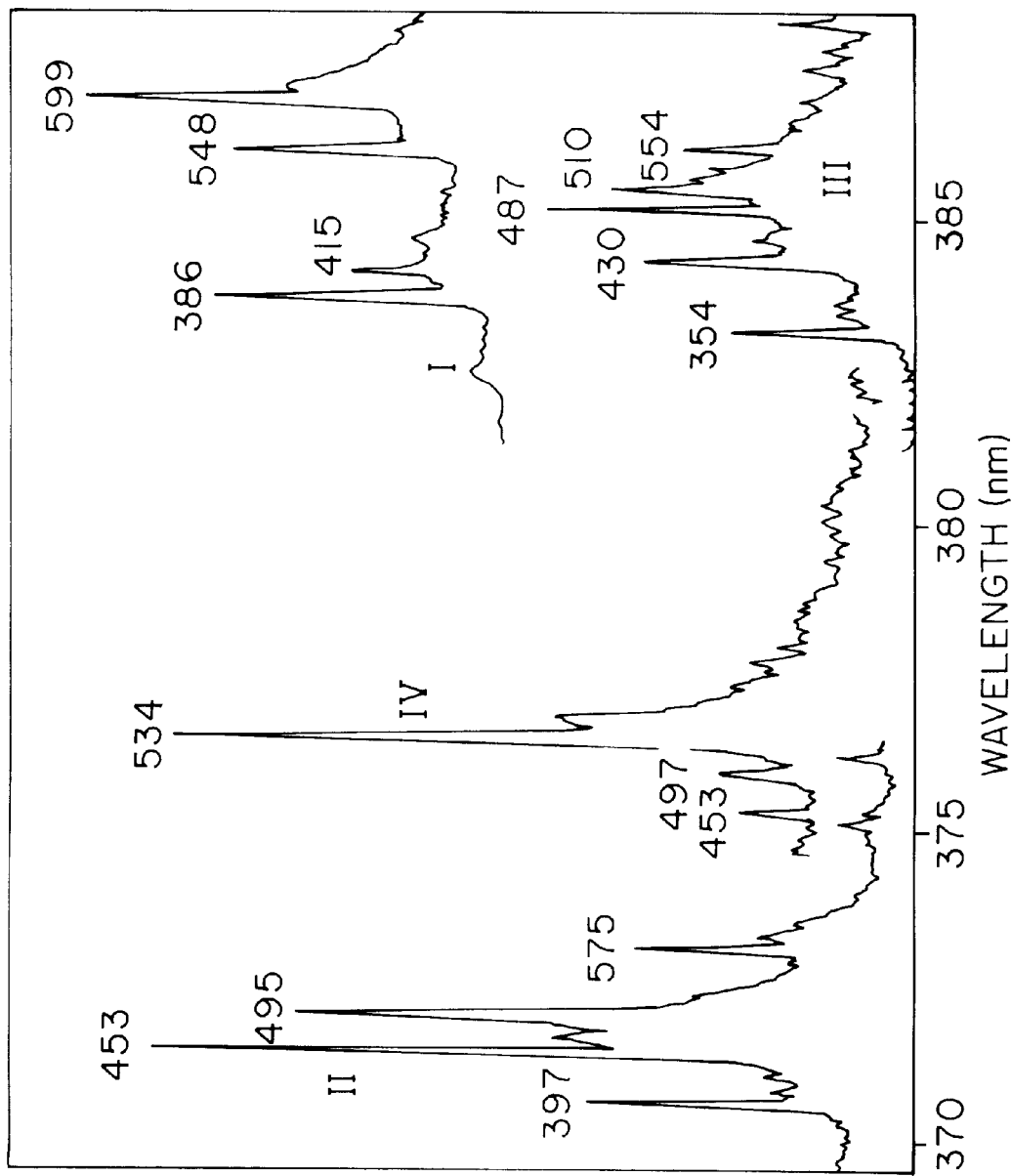
FIG. 5 depicts FLN spectra of the CE-separated analytes: 1-hydroxyprene (I), pyrene (II), B[a]A (III), B[e]P (IV). Laser excitation wavelength 365.2 nm, 369.0 nm, 3.78.0 nm, and 378.0 nm, respectively; T=4.2K. Peaks are labeled with their excited state vibrational frequencies, in $cm^{-1}$.

The NLN spectra do not provide sufficient detail to distinguish isomeric and other closely related compounds. Spectroscopic structural information can be obtained, however, from FLN spectra acquired using selective laser excitation at liquid helium temperature. Representative FLN spectra for CE-separated 1-hydroxypyrene, pyrene, B[a]A, and B[e]P are shown in FIG. 5. The spectra were obtained using excitation wavelengths of 369.0, 365.2, 378.0, and 378.0 nm, respectively. (An FLN spectrum for CE-separated B[a]P is identical to that shown in FIG. 3, spectrum (b), and therefore has not been included here.) The peaks in the FLN spectra are labeled with their excited state vibrational frequencies, in $cm^{-1}$. Each of these spectra provides a "fingerprint" fluorescence spectrum that can be used for spectral identification of the compound. Spectral resolution of 1-hydroxypyrene and B[a]A, difficult to achieve based on their NLN spectra, is trivial based on their FLN spectra because of differences in their excited state vibrational modes (compare spectra I and III in FIG. 5, acquired using the same excitation wavelength). By changing the laser excitation wavelength, a series of FLN spectra can be acquired, effectively characterizing all the excited state vibrational modes of the analyte. The series of "fingerprint" FLN spectra for a given compound provide the basis on which detailed spectroscopic structural information can be acquired by FLNS.

EXAMPLE II
Cooling Rate of the Capillary Cryostat
Materials and Methods

The components of the CE-FLN were substantially as described in Example I. Briefly, the system includes a modular CE apparatus (ATI Unicam model 310) coupled to a capillary cryostat (CC) and high-resolution spectrometer system. The CC is formed by a double-walled quartz cell with inlet and return lines for introducing liquid nitrogen or liquid helium; the outer portion of the CC is evacuated. The capillary, positioned in the central region of the CC, can be cooled to 77K or 4.2K after the CE separation is complete, by a continuous flow of liquid nitrogen or liquid helium through the cryostat.

For the separation of PAHs and PAH-DNA adducts discussed in Examples II through IV, an acetonitrile-water solution (30% v/v) containing 40 mM sodium bis(2-ethylhexyl) sulfosuccinate and 8 mM sodium borate, adjusted to pH 9 using phosphoric acid, was used as the CE buffer. Separation of analytes was achieved on the basis of micellar electrokinetic chromatography (MECC), with sodium bis(2-ethylhexyl) sulfosuccinate as the surfactant. UV-transparent fused silica capillary tubing (olymicro Technologies), 75 μm internal diameter (i.d.) and 95 cm long, wass used for electrophoretic separations. Samples were injected hydrodynamically, and separations were typically performed at an applied voltage of about 25 kV. An absorbance detector, positioned about 40 cm from the inlet of the capillary (not shown in FIG. 1), was incorporated to provide absorption electropherograms. Fluorescence electropherograms were obtained using either an excimer laser or argon-ion laser for excitation of the CE-separated analytes within the CC, approximately 85 cm from the capillary inlet. When the separation is complete, the voltage was turned off and the capillary is cooled to low temperature.

CE-separated analytes were characterized by low-temperature fluorescence spectroscopy. For FLN measurements, a 1 m focal-length monochromator (McPherson model 2061) was equipped with a 2400 G/mm grating, providing a resolution of 0.8 nm and a spectral window of approximately 10 nm. An excimer-pumped dye laser system (Lambda Physik LEXtra excimer and FL-2002 dye laser) was used for excitation. FLN spectra were generated using a series of laser wavelengths that selectively excite regions of the $S_1 \leftarrow S_0$ transition of the analyte, each of which reveals a portion of the excited-state vibrational frequencies of the molecule. Fluorescence was collected at a right angle to the laser excitation beam, dispersed by the monochromator, and detected by a photodiode array (Princeton Instruments IRY-1024/GRB intensified array); the diode array was operated in a gated detection mode, using the output of a photodiode to trigger a high-voltage pulse generator (Princeton Instruments FG-100). To discriminate against scattered and reflected laser light, the CC was tilted about 20° with respect to the laser beam. The CC was attached to a translation stage (New England Affiliated Technologies model TM-200-SM); translation of the CC and capillary allowed the CE-separated analytes to be sequentially characterized by NLN and FLN spectroscopy.

Cooling Rate of the Analytes

Figure 6:
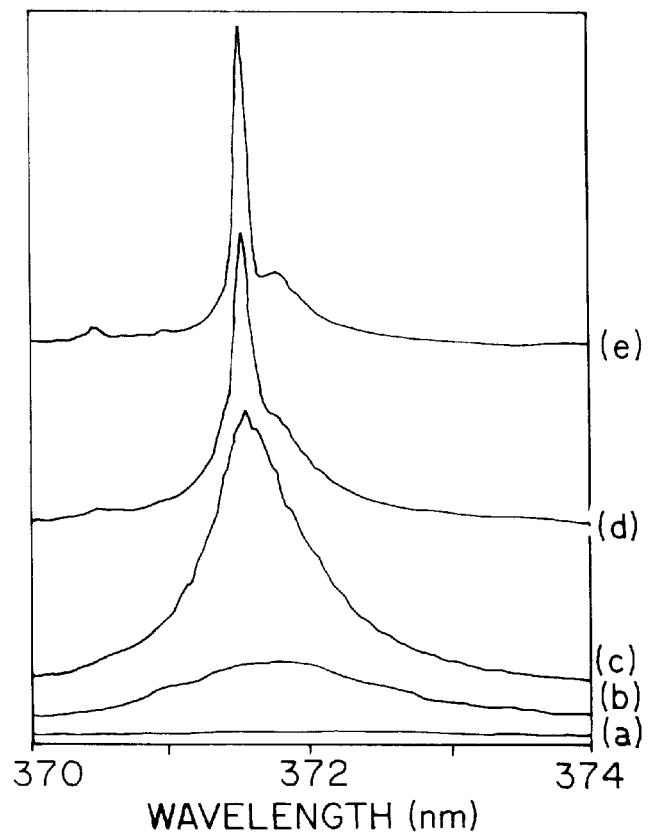
FIG. 6 depicts FLN spectra of pyrene as a function of time (temperature) after opening the valve of the helium transfer line to the capillary cryostat; $\lambda_{ex}$=369.6 nm. Spectrum (a) was obtained at room temperature and spectra (b)–(e) were obtained 30, 35, 40, and 50 seconds, respectively, after opening the valve of the helium transfer line.

The small dimensions of the capillary cryostat (4 mm i.d. and 22 cm in length) and the low thermal capacity of the capillary section to be cooled was expected to permit rapid cooling of analytes after the CE separation is complete. To evaluate the actual rate of cooling, fluorescence spectra of pyrene were acquired as a function of time after opening the valve of the helium transfer line to the CC (FIG. 6.) Spectrum (a) was obtained at room temperature, and spectra (b)–(e) were obtained 30, 35, 40, and 50 seconds after opening the valve. The five spectra, plotted using the same y-axis scale expansion (offset for clarity), illustrate a very fast cooling rate and a significant increase in fluorescence quantum yield with decreasing temperature. Spectrum (e), obtained at 50 seconds, is identical to the FLN spectrum of pyrene obtained in a regular helium immersion cryostat. This clearly indicates that the capillary and CC can be cooled to 4.2K in less than 1 minute. As a result, after the separation is complete, the CE-separated analytes can be rapidly frozen in place in the CC, leading to very minimal band dispersion. Once frozen, arbitrary detection times can be used to completely characterize the separated analytes. When the fluorescence analysis is complete, efficient warming of the CC and capillary can be achieved by closing the valve of the helium transfer line and introducing (warm) helium gas into the CC.

Figure 7A:
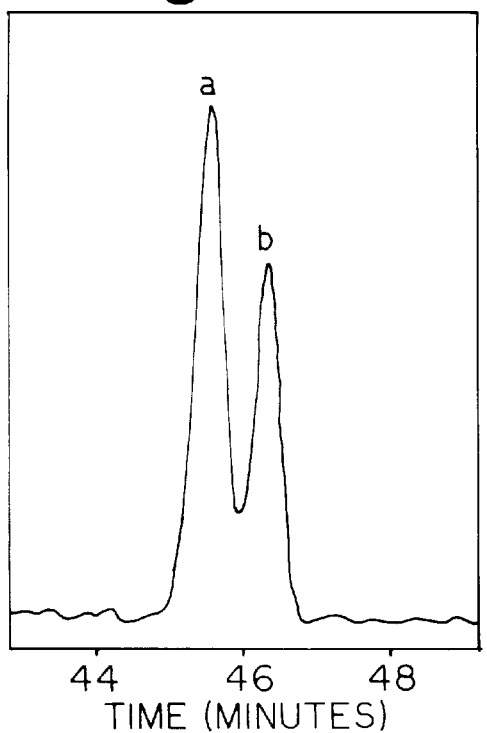
FIG. 7 depicts room temperature fluorescence electropherograms for a mixture of (a) B[a]P-$d_{12}$ and (b) B[a]P using a CE buffer consisting of 40 mM sodium bis(2-ethylhexyl) sulfosuccinate and 8 mM sodium borate in acetonitrilewater (30% v/v), pH 9; capillary, 75 $\mu$m i.d. and 85 cm length; applied voltage, 25 kV; current, 50 $\mu$A. FLN spectra in the CE-buffer matrix at T=4.2K, $\lambda_{ex}$=395.7 nm, were obtained for the CE-separated analytes (a) and (b). Spectra (c) and (d) are from the library of FLN spectra of PAHs for B[a]P-$d_{12}$ and B[a]P, respectively. The FLN peaks are labeled with their $S_1$ vibrational frequencies, in $cm^{-1}$.
Figure 7B:
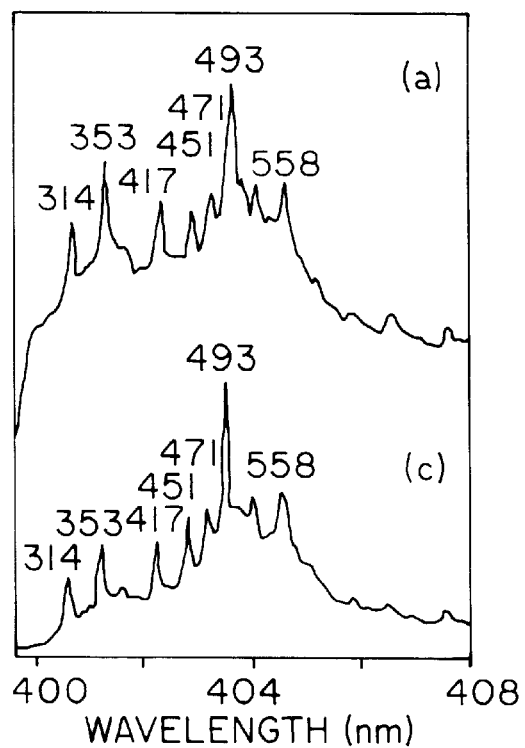
Figure 7C:
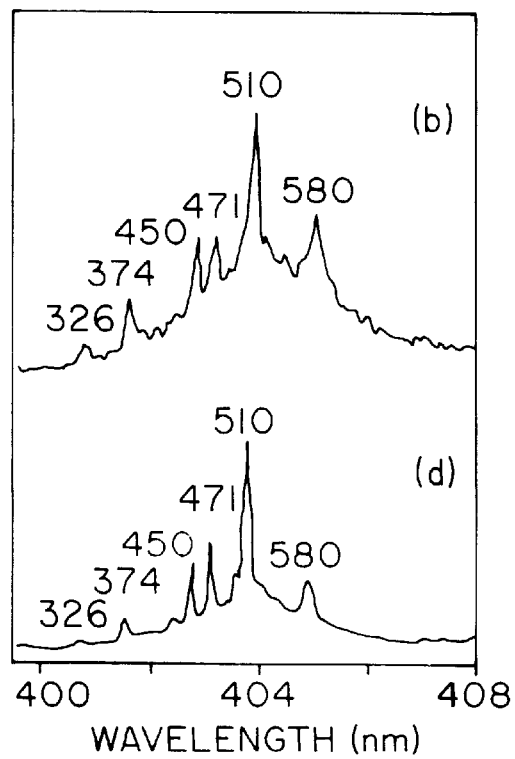

EXAMPLE III
CE-FLNS Analysis of Structurally Similar Compounds: Perprotio- and Perdeuterio-benzo[a]pyrenes Separation and spectral characterization of a mixture of deuterated and protonated benzo[a]pyrene (B[a]P) by CE-FLNS, as described in Example II, is shown in FIG. 7. Frame A is a portion of the room-temperature fluorescence electropherogram for the B[a]P-$d_{12}$/B[a]P mixture (c~$10^{-5}$ M), generated from a three-dimensional plot of fluorescence emission (intensity and wavelength) versus time. The excimer laser was used for excitation (308 $\mu$m), and the total fluorescence emission signal in the 350–500 nm region was integrated to generate the fluorescence electropherogram shown in FIG. 7A. The wavelengths of the fluorescence origin bands obtained for peaks (a) and (b) were 403 and 404 nnm, respectively.

FLN spectra for CE-separated peaks (a) and (b) using selective laser excitation at 395.7 mn at 4.2K are shown in FIG. 7, Frames B (spectrum a) and C (spectrum b), respectively. While some of the excited-state vibrational modes are similar in the two spectra, there are some obvious differences. For B[a]P-$d_{12}$, there are strong modes at 353, 493, and 558 cm$^{-1}$; for B[a]P, the strong modes are at 510 and 580 cm$^{-1}$. Thus, spectra (a) and (b) are clearly distinguishable with a different pattern of vibrational frequencies and intensities, revealing differences in analyte composition. These data (and other FLN spectra obtained using different laser excitation wavelengths) can be used as "fingerprints" for spectral identification of a compound. The identity of CE-separated analytes is obtained by comparison of the FLN spectra acquired with the available library of FLN spectra for PAHs. Comparison of the CE-FLN spectra in FIG. 7 shows that spectrum (a) is virtually indistinguishable from spectrum (c), the B[a]P-$d_{12}$ standard, and spectrum (b) is identical to spectrum (d), the B[a]P standard. Therefore, peaks (a) and (b) of the electropherogram can be unambiguously assigned as deuterated B[a]P and protonated B[a]P, respectively. Thus, deuteration leads to a blue-shift in the fluorescence spectra of PAHs, as has been shown for perylene and B[a]P in n-octane Shpol'skii matrices. The fact that the migration time for B[a]P-$d_{12}$ is shorter than that for B[a]P in FIG. 7A is consistent with previous MECC separations of dansylated methylamine and dansylated methyl-$d_3$-amine, and indicates that the deuterated analog is more hydrophilic than the protonated compound.

EXAMPLE IV
Analysis of Incompletely Separated Analytes

Figure 8A:
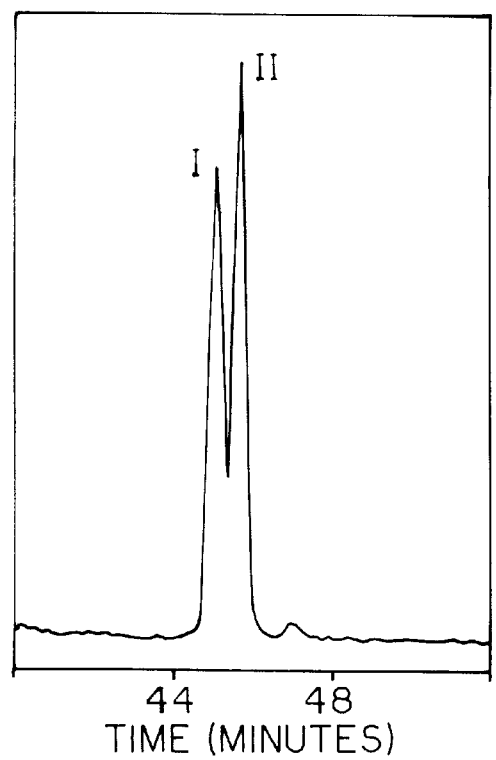
FIG. 8 depicts (A) room-temperature fluorescence electropherogram for a mixture of (I) B[e]P and (I) B[a]P; (B) FLN spectra of CE-separated B[e]P (I) obtained in the CE-buffer matrix at T=4.2K using $\lambda_{ex}$=369.0 nm (upper) and $\lambda_{ex}$=365.8 nm (lower spectrum); and (C) FLN spectra of CE-separated B[a]P (II) obtained in the CE-buffer matrix at T=4.2K using $\lambda_{ex}$=395.7 nm (upper) and $\lambda_{ex}$=393.8 nm (lower spectrum). The FLN peaks are labeled with their $S_1$ vibrational frequencies, in $cm^{-1}$.
Figure 8B:
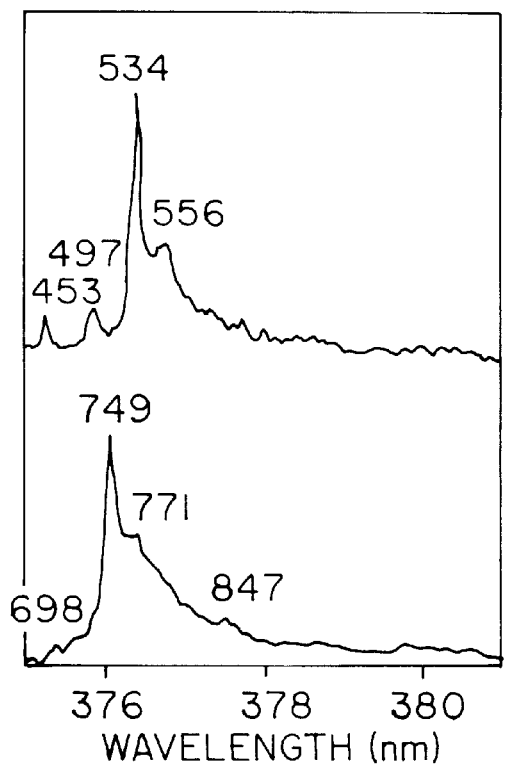
Figure 8C:
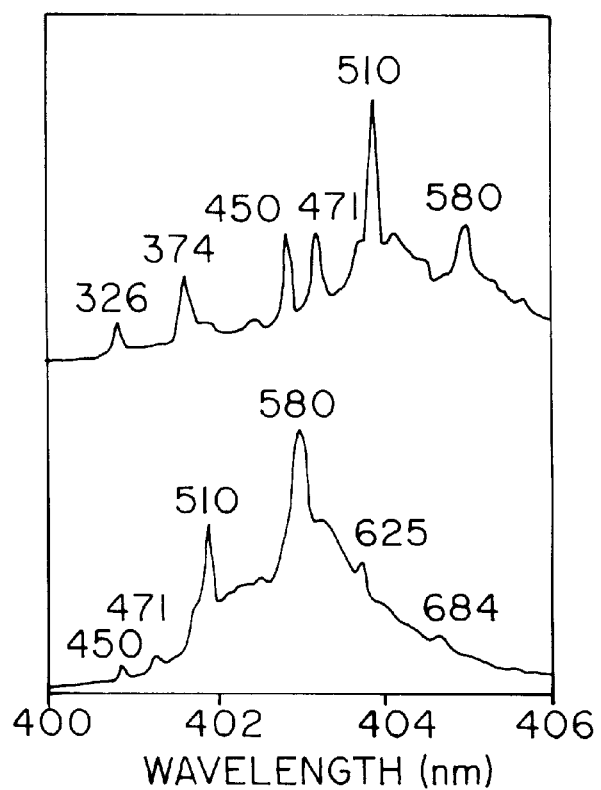
Figure 9A:
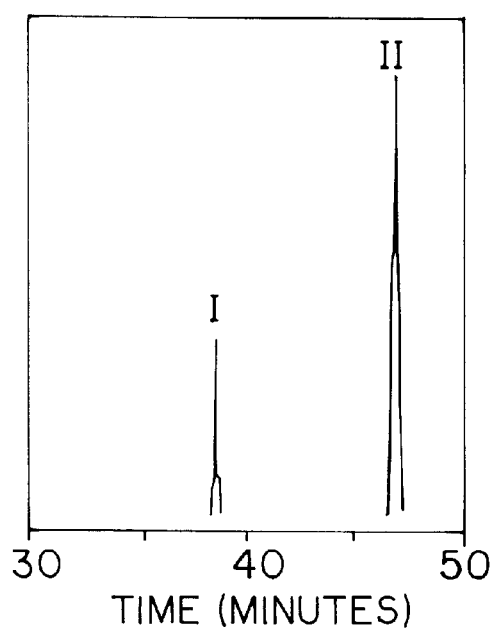
FIG. 9 depicts room temperature fluorescence electropherograms (Frames A and B) obtained for two different DBP-N3Ade adduct samples. FLN spectra for the CE-separated analytes (I and II) are shown in Frames C and D using $\lambda_{ex}$=416.0 nm; T=4.2K. The FLN peaks are labeled with their $S_1$ vibrational frequencies, in $cm^{-1}$. See text for discussion.
Figure 9B:
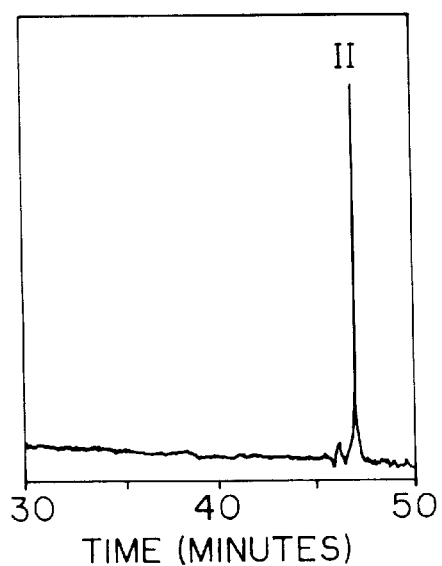
Figure 9C:
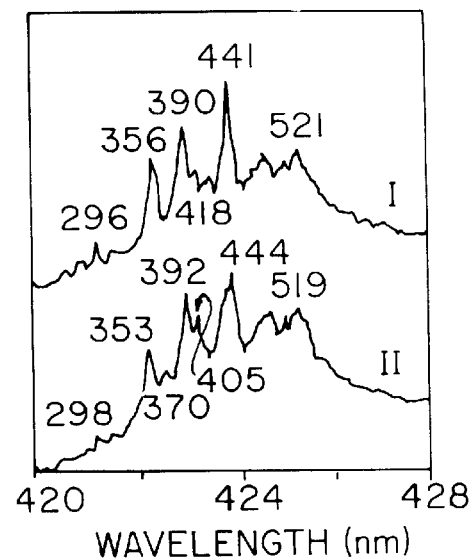
Figure 9D:
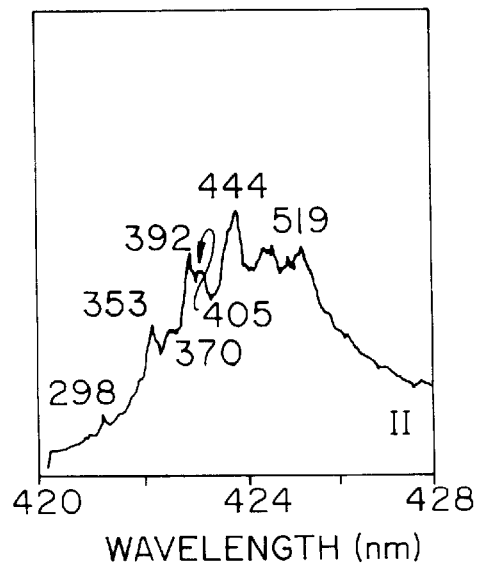

An example of the CE-FLN analysis of incompletely resolved analytes is shown in FIG. 8 for a mixture of benzo[e]pyrene (B[e]P) and B[a]P. See Example II for description of the experimental procedures used. The fluorescence electropherogram in Frame A shows that these two isomers are not baseline-resolved in the CE separation. Low-temperature fluorescence detection revealed the presence of two analytes via two distinct fluorescence origin bands at 376 nm and 403 nm, respectively. This would also be the case if the analytes were not separated (i.e. if B[e]P and B[a]P comigrated). CE-FLN spectra for B[e]P and B[a]P are shown in FIG. 8, Frames B and C, respectively. Since the (0,0) band for B[e]P is located at 376 nm, selective laser excitation in the range of approximately 371–357 nm (~350–1400 cm$^{-1}$ above the origin band) can be used to generate FLN spectra for B[e]P; two of these are shown in FIG. 8B. For B[a]P, which has its (0,0) band at 403 nm, selective laser excitation in the 397–381 nm range can be used to generate FLN spectra; two of these are shown in FIG. 4C. By changing the laser excitation wavelength, a series of FLN spectra can be obtained that map out all of the excited-state vibrational frequencies of the molecule. It is this series of fingerprint FLN spectra that provides selective, unambiguous structural characterization of fluorescent analytes. It is thus demonstrated that in some cases the selectivity of FLNS alone is sufficient to characterize mixtures of analytes, even if they are not completely resolved in the CE separation.

EXAMPLE V
Confirmation of Analyte Purity

An application of the CE-FLNS system in the area of confirmation of analyte purity is shown in FIG. 9. See Example II for a description of the experimental procedures used. Fluorescence electropherograms for two different samples of a dibenzo[a,l]pyrene-adenine adduct (3-(dibenzo [a,l]pyren-10-yl)-adenine; DBP-N3Ade) are shown in Frames A and B. Both of these samples had been subjected to purification by two-dimensional HPLC and were then analyzed by CE-FLNS. For sample 1 (Frame A), there are two major peaks (I and II) plus a number of smaller, minor contaminants. For sample 2 (Frame B), the electropherogram shows the presence of only one prominent peak (II). FLN spectra obtained at 4.2K using 416.0 nm excitation for the major peaks are shown in Frames C and D. The FLN spectra for analyte II in both samples match the spectra of a DBP-N3Ade standard adduct, whose structure had been confirmed by MS. Thus analyte II can be assigned as the DBP-N3Ade adduct. The FLN spectra for analyte I show a different pattern of vibrational frequencies and intensities, so analyte I cannot be DBP-N3Ade. Although the identity of analyte I has not been determined, it is more hydrophilic than DBP-N3Ade (based on the CE retention times) yet possesses a substituted DBP fluorescent chromophore (based on the FLN spectra). This example shows that on-line characterization by CE-FLNS affords a number of advantages compared to HPLC separation, fraction collection, and subsequent (off-line) analysis. Imprecise timing of fraction collection, leading to impure HPLC fractions, is likely responsible for the differences in these two DBP N3Ade samples. As shown in FIG. 9, on-line analysis by CE-FLNS, combining the high resolving power of CE and the spectral selectivity of FLNS, provides an excellent method to determine the purity of analytes and analyte fractions.

EXAMPLE VI
Analysis of Structurally Similar DNA Adducts

Figure 10A:
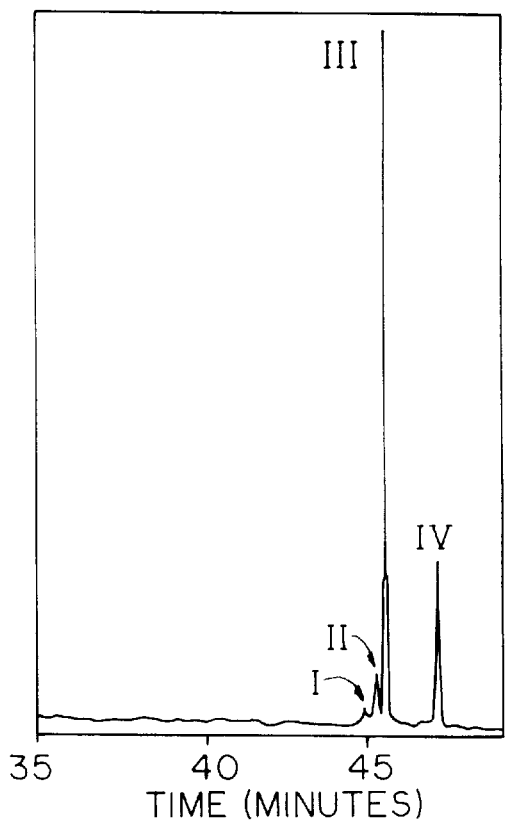
FIG. 10 depicts a room-temperature fluorescence electropherogram obtained during separation of a mixture of (II) DBP-N7Ade, (III) DPB-N1Ade, and (IV) DPB-N3Ade. An unidentified impurity is labeled as peak (I). (B) FLN spectra for the three CE-separated adducts, obtained at 4.2K using selective laser excitation at 416.0 nm. The FLN peaks are labeled with their $S_1$ vibrational frequencies, in cm$^{-1}$.
Figure 10B:
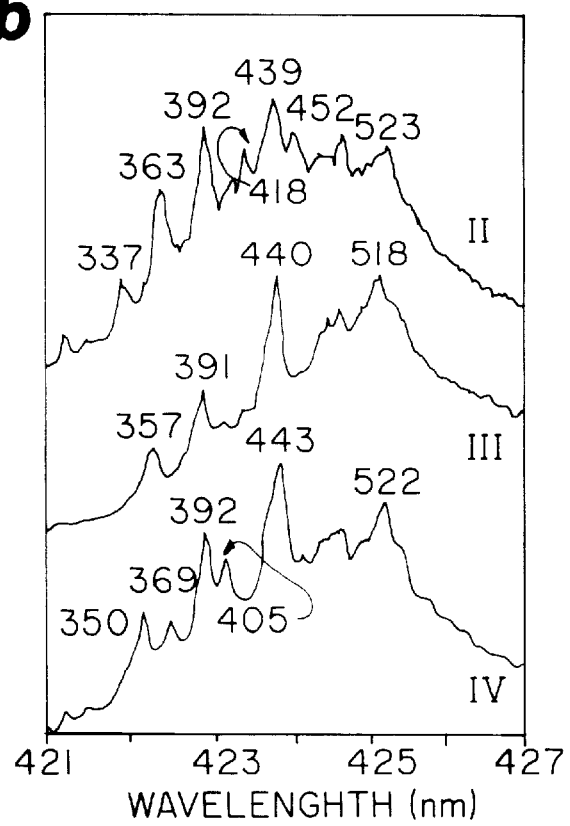

Another example of the selective detection provided by the combination of the separation power of CE and the spectral selectivity of FLNS is shown in FIG. 10 for the analysis of three dibenzo[a,l]pyrene-adenine adducts, DBP-N1Ade (1-(dibenzo[a,l]pyren-10-yl)-adenine), DBP-N3Ade (3-(dibenzo[a,l]pyren-10-yl)-adenine), and DBP-N7Ade (7-(dibenzo[a,l]pyren-10-yl)-adenine). See Example II for the experimental procedures used. Since these three adducts differ only in the position at which binding of DBP to adenine occurs, they are structurally very similar. Previous FLNS analysis of these three DBP-adenine adducts resulted in selective identification of the individual adducts; that is, the individual adducts could be distinguished (unpublished results). However, a mixture of these adducts could not be resolved by FLNS alone. By combining CE (for separation) and FLNS (for spectral characterization), a mixture of these three adducts can be resolved, as shown in FIG. 10. The room-temperature fluorescence electropherogram obtained during CE separation of the DBP-adenine adduct mixture is shown in Frame A. Four peaks (labeled I, II, III, and IV) are observed, indicating that one is an impurity present in the mixture. CE-FLN spectra obtained for the three major separated analytes (II, III, and IV) are shown in FIG. 10B. These spectra were obtained in the CE buffer matrix at 4.2K, using selective laser excitation at 416.0 nm. Comparison of the FLN spectra in FIG. 10 with the library of FLN spectra generated for DNA adducts obtained in the CE buffer matrix in a regular helium immersion dewar showed that peaks II, III, and IV correspond to DBP-N7Ade, DBP-N1Ade, and DBP-N3Ade, respectively. Since the adducts of interest were identified, no attempt was made to characterize the impurity peak (I).

The preceding examples demonstrate that FLNS can be interfaced with CE for on-line detection and spectroscopic identification of molecular analytes. The major technical challenges of design and fabrication of a compact and reliable liquid helium capillary cryostat (CC) and precise translation of the CC and capillary over large distances have been overcome. Of equal importance was the finding that solidification of the CE buffer yields glassy matrices required for FLNS.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A system for use in capillary electrophoresis comprising:
   (a) a capillary cryostat comprising:
      (i) a capillary comprising a transparent annular wall forming an interior portion therein for placement of a target species; and
      (ii) a capillary encasement comprising a transparent portion, wherein at least a portion of the transparent annular wall of said capillary is surrounded by the transparent portion of the capillary encasement to form an optically accessible sample chamber;
   (b) a spectrally narrow excitation source positioned to direct a beam of light into the interior portion of the capillary to induce fluorescence emission from the target species; and
   (c) a wavelength-dispersive detection system positioned to detect fluorescence emission from the target species.

2. The system of claim 1 wherein the capillary cryostat is mounted on a translational stage capable of translating the sample chamber along the longitudinal capillary axis relative to the spectrally narrow excitation source.

3. The system of claim 1 wherein the capillary encasement comprises a first transparent annular wall and a second transparent annular wall having an annular lumen therebetween, wherein the annular lumen functions as a thermal barrier.

4. The system of claim 3 wherein the second transparent annular wall of the capillary encasement forms an inner lumen surrounding the portion of the transparent annular wall of said capillary that is surrounded by the transparent portion of the capillary encasement.

5. The system of claim 4 wherein the inner lumen contains a cryogen.

6. The system of claim 1 wherein the wavelength-dispersive detection system comprises a high resolution monochromator and a detector.

7. A system for use in capillary electrophoresis comprising:
   (a) a capillary cryostat comprising:
      (i) a capillary comprising a transparent annular wall forming an interior portion therein for placement of a target species;
      (ii) a capillary encasement comprising a transparent portion, wherein at least a portion of the transparent annular wall of said capillary is surrounded by the transparent portion of the capillary encasement to form an optically accessible sample chamber;
      (iii) an inlet portion in fluid communication with a first end of the capillary encasement for delivery of a cryogen to the optically accessible sample chamber; and
      (iv) an outlet portion in fluid communication with second end of the capillary encasement for elimination of the cryogen from the optically accessible sample chamber;
   (b) a laser positioned to direct a beam of light into the interior portion of the capillary to induce fluorescence emission from the target species; and
   (c) a wavelength-dispersive detection system positioned to detect fluorescence emission from the target species.

8. The system of claim 7 wherein the wavelength-dispersive detection system comprises a high resolution monochromator and a detector selected from the group consisting of a diode array detector and an image array detector.

9. A system for use in capillary electrophoresis comprising:
   (a) a capillary cryostat comprising:
      (i) a capillary comprising a transparent annular wall forming an interior portion therein for placement of a target species; and
      (ii) a capillary encasement comprising a transparent portion, wherein at least a portion of the transparent annular wall of said capillary is surrounded by the transparent portion of the capillary encasement to form an optically accessible sample chamber;
   (b) a laser positioned to direct a beam of light into the interior portion of the capillary to induce emission from the target species; and
   (c) a wavelength-dispersive detection system positioned to detect fluorescence emission from the target species, wherein the wavelength-dispersive detection system comprises a high resolution monochromator and a detector selected from the group consisting of a diode array detector and an image array detector.

10. A capillary cryostat comprising:
(a) a capillary comprising a transparent annular wall forming an interior portion therein for placement of a target species;
(b) a capillary encasement comprising a transparent portion, wherein at least a portion of the transparent annular wall of said capillary is surrounded by the transparent portion of the capillary encasement to form an optically accessible sample chamber;
(c) a delivery line operatively connected to the capillary encasement at an inlet end;
(d) an exit line operatively connected to the capillary encasement at an outlet end; and
(e) a stress relief means proximal to the inlet end of the capillary encasement for reducing turbulence of a cryogen entering the capillary encasement.

11. The capillary cryostat of claim 10 wherein an entry segment operatively connects the delivery line to the inlet end of the capillary encasement.

12. The capillary cryostat of claim 11 wherein the entry segment comprises a diverter such that a cryogen is directed from a path substantially parallel to a delivery line axis to a path substantially normal to the delivery line axis.

13. The capillary cryostat of claim 11 wherein the entry segment comprises a first cold tube seal comprising a material having a coefficient of thermal expansion substantially similar to a material forming the capillary encasement.

14. The capillary cryostat of claim 13, wherein the first cold tube seal is sealingly attached to an inlet end of the inner annular wall of the capillary encasement.

15. The capillary cryostat of claim 10 wherein an exhaust segment operatively connects the exit line to the outlet end of the capillary encasement.

16. The capillary cryostat of claim 15 wherein the exhaust segment comprises a second cold tube seal comprising a material having a coefficient of thermal expansion substantially similar to a material forming the capillary encasement.

17. The capillary cryostat of claim 16 wherein the second cold tube seal is sealingly attached to an outlet end of the inner annular wall of the capillary encasement.

18. The capillary cryostat of claim 15 wherein a thermal contraction bellow operatively connects the exhaust segment to the exit line.

19. The capillary cryostat of claim 18 wherein the exhaust segment further comprises an axial stress relief bellow oriented in a direction substantially parallel to the capillary encasement.

20. A method for performing capillary electrophoresis of a sample containing a fluorescent target species comprising:
(a) providing a capillary cryostat comprising:
  (i) a capillary comprising a transparent annular wall; and
  (ii) a capillary encasement comprising a transparent annular wall forming a lumen therein, wherein at least a portion of the transparent annular wall of said capillary is within the lumen surrounded by the transparent portion of the capillary encasement to form an optically accessible sample chamber;
(b) electrophoresing the sample through the capillary to position the target species in the optically accessible sample chamber;
(c) freezing the target species by introducing a cryogen into the lumen of the capillary encasement;
(d) irradiating the frozen target species to induce fluorescence emission from target species; and
(e) detecting the fluorescence emission.

21. The method of claim 20 wherein the cryogen of step (c) is a cryogenic fluid selected from the group consisting of liquid nitrogen, cold nitrogen vapor, liquid helium, and cold helium vapor.

22. The method of claim 21 wherein step (e) comprises obtaining at least one fluorescence non-line narrowing (NLN) spectrum.

23. The method of claim 20 wherein the cryogen is liquid helium.

24. The method of claim 23 wherein step (e) comprises obtaining at least one fluorescence line narrowing (FLN) spectrum.

25. A method for performing capillary electrophoresis of a sample containing a fluorescent target species comprising:
(a) providing a capillary cryostat comprising:
  (i) a capillary comprising a transparent annular wall; and
  (ii) a capillary encasement comprising a transparent annular wall forming a lumen therein, wherein at least a portion of the transparent annular wall of said capillary is within the lumen surrounded by the transparent portion of the capillary encasement to form an optically accessible sample chamber;
(b) filling the capillary with an eluant that forms a disordered matrix upon freezing;
(c) electrophoresing the sample through the capillary to position the target species in the optically accessible sample chamber;
(d) freezing the target species by introducing liquid helium into the lumen of the capillary encasement;
(e) irradiating the frozen target species with a laser to induce fluorescence emission from target species; and
(f) detecting the fluorescence emission using fluorescence line-narrowing (FLN) spectroscopy.

26. The method of claim 25 step (f) comprises obtaining at least one FLN spectrum, and wherein the method further comprises step (g) analyzing the at least one FLN spectrum to obtain structural information about the fluorescent target species.

27. The method of claim 25 wherein the target species comprises a polyaromatic hydrocarbon (PAH).

28. A method for performing capillary electrophoresis of a sample containing a fluorescent target species comprising:
(a) providing a capillary cryostat comprising:
  (i) a capillary comprising a transparent annular wall; and
  (ii) a capillary encasement comprising a transparent annular wall forming a lumen therein, wherein at least a portion of the transparent annular wall of said capillary is within the lumen surrounded by the transparent portion of the capillary encasement to form an optically accessible sample chamber;
(b) filling the capillary with an eluant that forms a disordered matrix upon freezing;
(c) electrophoresing the sample through the capillary to position the target species in the optically accessible sample chamber;
(d) freezing the target species by introducing liquid nitrogen into the lumen of the capillary encasement;
(e) irradiating the frozen target species with a laser to induce fluorescence emission from target species;

(f) detecting the fluorescence emission using non line-narrowing spectroscopy;
(g) removing the liquid nitrogen from the lumen of the capillary encasement;
(h) introducing liquid helium into the lumen of the capillary encasement;
(i) irradiating the frozen target species with a laser to induce fluorescence emission from target species; and
(j) detecting the fluorescence emission using fluorescence line-narrowing (FLN) spectroscopy.

29. The method of claim 28 further comprising (k) analyzing the fluorescence emissions detected in step (f) and step (j) to obtain structural information about the target species.

* * * * *